US012157083B2

(12) United States Patent
Narihata

(10) Patent No.: US 12,157,083 B2
(45) Date of Patent: Dec. 3, 2024

(54) PARTICULATE COLLECTION DEVICE

(71) Applicant: Panasonic Intellectual Property Management Co., Ltd., Osaka (JP)

(72) Inventor: Koki Narihata, Kyoto (JP)

(73) Assignee: INTELLECTUAL PROPERTY MANAGEMENT CO., LTD., Osaka (JP)

(*) Notice: Subject to any disclaimer, the term of this patent is extended or adjusted under 35 U.S.C. 154(b) by 624 days.

(21) Appl. No.: 17/368,985

(22) Filed: Jul. 7, 2021

(65) Prior Publication Data

US 2021/0331113 A1 Oct. 28, 2021

Related U.S. Application Data

(63) Continuation of application No. PCT/JP2020/007020, filed on Feb. 21, 2020.

(30) Foreign Application Priority Data

Mar. 28, 2019 (JP) ................................ 2019-064569
Mar. 28, 2019 (JP) ................................ 2019-064604

(51) Int. Cl.
*B01D 46/44* (2006.01)
*B01D 46/00* (2022.01)
(Continued)

(52) U.S. Cl.
CPC ....... *B01D 46/442* (2013.01); *B01D 46/0056* (2013.01); *B01D 46/4263* (2013.01);
(Continued)

(58) Field of Classification Search
CPC .............. B01D 46/442; B01D 46/0056; B01D 46/4263; B01D 46/62; B01D 46/79;
(Continued)

(56) References Cited

U.S. PATENT DOCUMENTS 1,075,736 A * 10/1913 Name not available .................... B01D 45/14 55/400
3,763,631 A * 10/1973 Horn ...................... B01D 46/10 95/215
(Continued)

FOREIGN PATENT DOCUMENTS

CN 107441847 A * 12/2017
DE 102004048539 A1 * 4/2006 ............ F01M 13/04
(Continued)

OTHER PUBLICATIONS

International Search Report of PCT application No. PCT/JP2020/007020 dated Apr. 21, 2020.
(Continued)

*Primary Examiner* — Stephen Hobson
(74) *Attorney, Agent, or Firm* — Wenderoth, Lind & Ponack, L.L.P.

(57) ABSTRACT

A particulate collector includes a housing having an air intake port and an exhaust port and a flow channel, in the housing, connecting the two ports, a fan rotatable about an R-axis to generate airflow in the flow channel, a spray unit that sprays first liquid into a first portion in the flow channel, a first filter located between the first portion and the exhaust port and supported rotatably about the R-axis, a power source that rotates the first filter, a first collection port for collecting a first particulate covered with liquid contained in the first liquid from the flow channel through a second portion in the first filter, and a second collection port for collecting a second particulate covered with liquid contained in the first liquid from the flow channel through a third portion in the first filter. The second portion is located between the first and third portions.

7 Claims, 13 Drawing Sheets

(51) Int. Cl.
*B01D 46/42* (2006.01)
*B01D 46/62* (2022.01)
*B01D 46/79* (2022.01)
*B01D 47/06* (2006.01)

(52) U.S. Cl.
CPC ............. *B01D 46/62* (2022.01); *B01D 46/79* (2022.01); *B01D 47/06* (2013.01); *B01D 46/0005* (2013.01)

(58) Field of Classification Search
CPC .... B01D 47/06; B01D 46/0005; B01D 46/10; B01D 2273/30; B01D 46/003; B01D 45/14; B01D 50/20; B01D 51/04; A61L 9/14; A61L 9/16; B07B 7/083; B07B 11/04; B07B 11/08
See application file for complete search history.

(56) References Cited

U.S. PATENT DOCUMENTS

| | | | | | |
|---|---|---|---|---|---|
| 3,860,403 | A * | 1/1975 | Aoi | F01N 3/038 | 55/319 |
| 4,135,898 | A * | 1/1979 | Rosengard | B01D 59/20 | 55/459.2 |
| 4,189,310 | A * | 2/1980 | Hotta | B01D 46/26 | 55/400 |
| 4,994,097 | A * | 2/1991 | Brouwers | B04C 9/00 | 55/408 |
| 6,033,450 | A * | 3/2000 | Krul | B01D 45/14 | 55/438 |
| 6,251,168 | B1 * | 6/2001 | Birmingham | B01D 45/08 | 55/330 |
| 6,363,923 | B1 * | 4/2002 | Pletschacher | B04B 5/08 | 123/585 |
| 6,627,166 | B1 * | 9/2003 | Simon | B01D 50/20 | 422/123 |
| 7,833,298 | B2 * | 11/2010 | Larnholm | B01D 45/12 | 55/482 |
| 7,857,879 | B2 * | 12/2010 | Egger | B01D 45/08 | 55/423 |
| 9,168,475 | B2 * | 10/2015 | Dorao | B01D 45/14 | |
| 9,233,325 | B2 * | 1/2016 | Carlsson | B04B 5/12 | |
| 2006/0225386 | A1 * | 10/2006 | Brouwers | C10L 3/102 | 55/319 |
| 2009/0301296 | A1 * | 12/2009 | Hoijtink | B01D 19/0052 | 95/35 |
| 2011/0083558 | A1 * | 4/2011 | Van Der Vaart | B01D 45/14 | 95/267 |
| 2012/0151887 | A1 * | 6/2012 | Dorao | B01D 45/14 | 55/447 |
| 2016/0047342 | A1 * | 2/2016 | Kraxner | F02M 35/0201 | 55/442 |
| 2017/0274391 | A1 * | 9/2017 | Akasaka | B01D 45/12 | |
| 2023/0330580 | A1 * | 10/2023 | Fernandino | B01D 46/0031 | |

FOREIGN PATENT DOCUMENTS

| | | | |
|---|---|---|---|
| JP | 2996955 | 1/2000 | |
| JP | 2000-042350 | 2/2000 | |
| JP | 2006-289272 | 10/2006 | |
| JP | 2015-202425 | 11/2015 | |
| WO | WO-2016163075 A1 * | 10/2016 | B04B 5/12 |

OTHER PUBLICATIONS

English Translation of Search Report issued Oct. 10, 2022 in corresponding Chinese Patent Application No. 202080006343.2.
Extended European Search Report issued Apr. 29, 2022 in corresponding European Patent Application No. 20777132.0.

* cited by examiner

PARTICULATE COLLECTION DEVICE

BACKGROUND

1. Technical Field

The present disclosure relates to a particulate collection device that collects particulates in a gas.

2. Description of the Related Art

An example of an existing air purification device is capable of purifying polluted air using gas adsorption based on the principle of nuclear condensation. For example, an air purification device described in Japanese Unexamined Patent Application Publication No. 2000-42350 includes a heating unit, a heating humidification unit, a cooling humidification unit, a cooling unit, and a reheating unit provided in this order along an air flow channel. In addition, an eliminator is provided downstream of the cooling unit. In this manner, gas adsorption in the nuclear condensation growth process is facilitated and, thus, the efficiency of removing harmful gas can be increased. Furthermore, the inertial dust collection action of the eliminator enables discharge of condensate water.

SUMMARY

However, in the existing technology described above, a large amount of energy is consumed by the heating unit, heating humidification unit, cooling humidification unit, cooling unit, and reheating unit, and the size of the device needs to be increased.

One non-limiting and exemplary embodiment provides a particulate collection device capable of achieving size reduction, energy saving, and high collection speed.

In one general aspect, the techniques disclosed here feature a particulate collection device including a housing having an air intake port and an exhaust port and a flow channel connecting the air intake port to the exhaust port in the housing, a fan that generates, in the flow channel, airflow for drawing, from the air intake port into the flow channel, a gas containing a first particulate and a second particulate smaller than the first particulate, the fan being rotatable about a first axis, a spray unit that sprays a first liquid into a first portion included in the flow channel to coat the first particulate with liquid contained in the first liquid and coat the second particulate with liquid contained in the first liquid, a first filter located between the first portion and the exhaust port and supported rotatably about the first axis, a power source that rotates the first filter, a first collection port used to collect the first particulate coated with the liquid contained in the first liquid from the flow channel through a second portion included in the first filter, and a second collection port used to collect the second particulate coated with the liquid contained in the first liquid from the flow channel through a third portion included in the first filter. The second portion is located between the first portion and the third portion.

According to an aspect of the present disclosure, a particulate collection device is capable of achieving size reduction, energy saving, and high collection speed.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
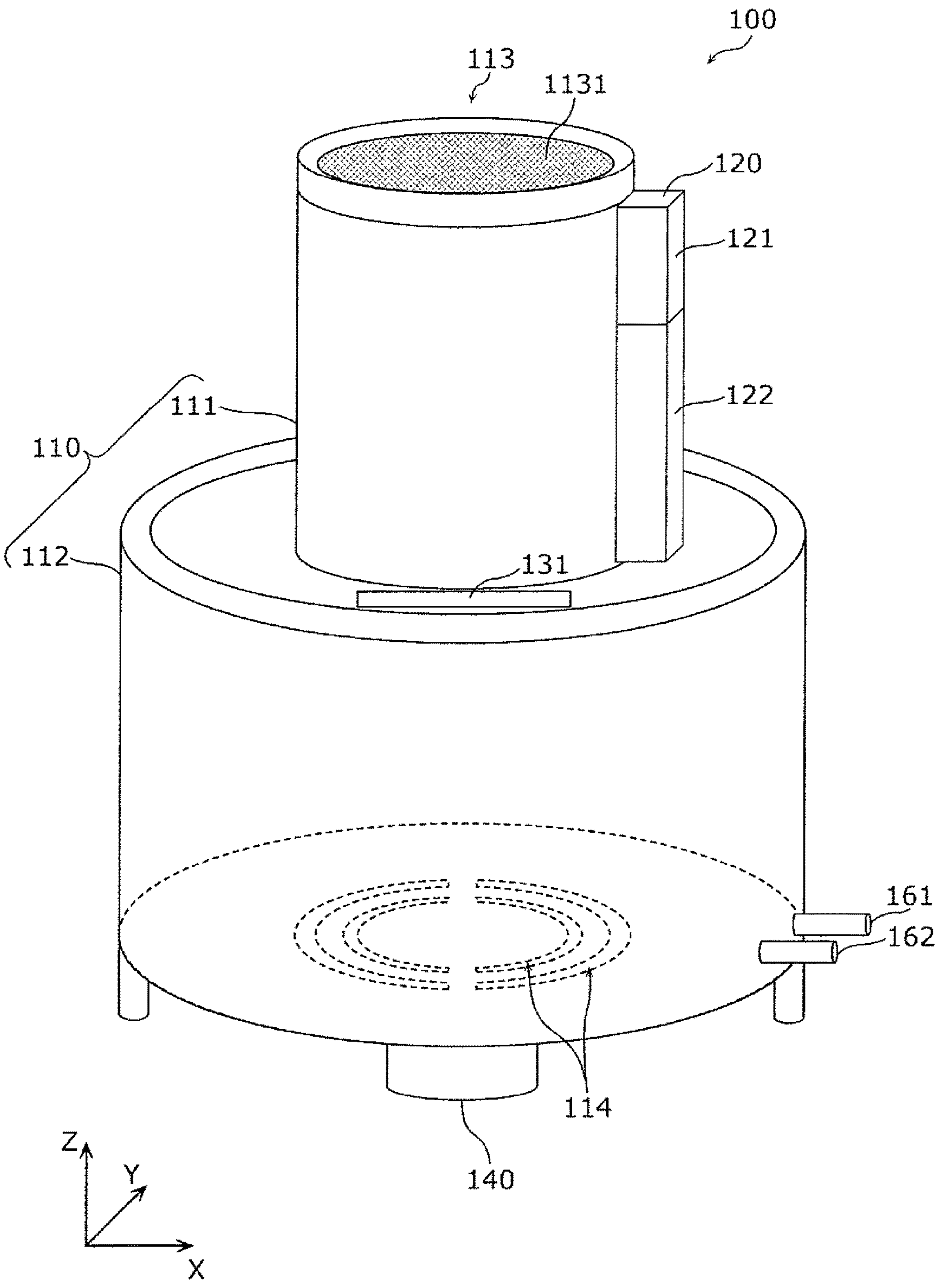
FIG. 1 is a perspective view of a particulate collection device according to Embodiment 1.

Embodiments are described below with reference to the accompanying drawings.

Note that each of the embodiments described below is a general or specific example of the present disclosure. A value, a shape, a material, a constituent element, the positions and the connection form of the constituent elements, steps, and the sequence of steps described in the embodiments are only examples and shall not be construed as limiting the scope of the present disclosure. In addition, among the constituent elements in the embodiments described below, the constituent element that does not appear in an independent claim, which has the broadest scope, is described as an optional constituent element. Furthermore, all the drawings are schematic and not necessarily to scale. The same reference numerals are used throughout the accompanying drawings to refer to substantially the same constituent elements, and duplicate descriptions may be eliminated or simplified.

As used herein, the terms describing the positional relationship between elements, such as “parallel” or “perpendicular”, the terms describing the shape of an element, such as “circular” or “rectangular”, and numerical ranges are not used in a strict sense but used in a broader sense (in a substantially equivalent range, for example, with a tolerance of several %).

In the drawings described below, the X- and Y-axes are mutually orthogonal axes in a horizontal plane. The Z-axis is an axis perpendicular to the horizontal plane. In terms of the Z-axis, a positive direction is upward, and a negative direction is downward.

Embodiment 1

Embodiment 1 is described below with reference to FIGS. 1 to 6.

Configuration of Particulate Collection Device

Figure 2:
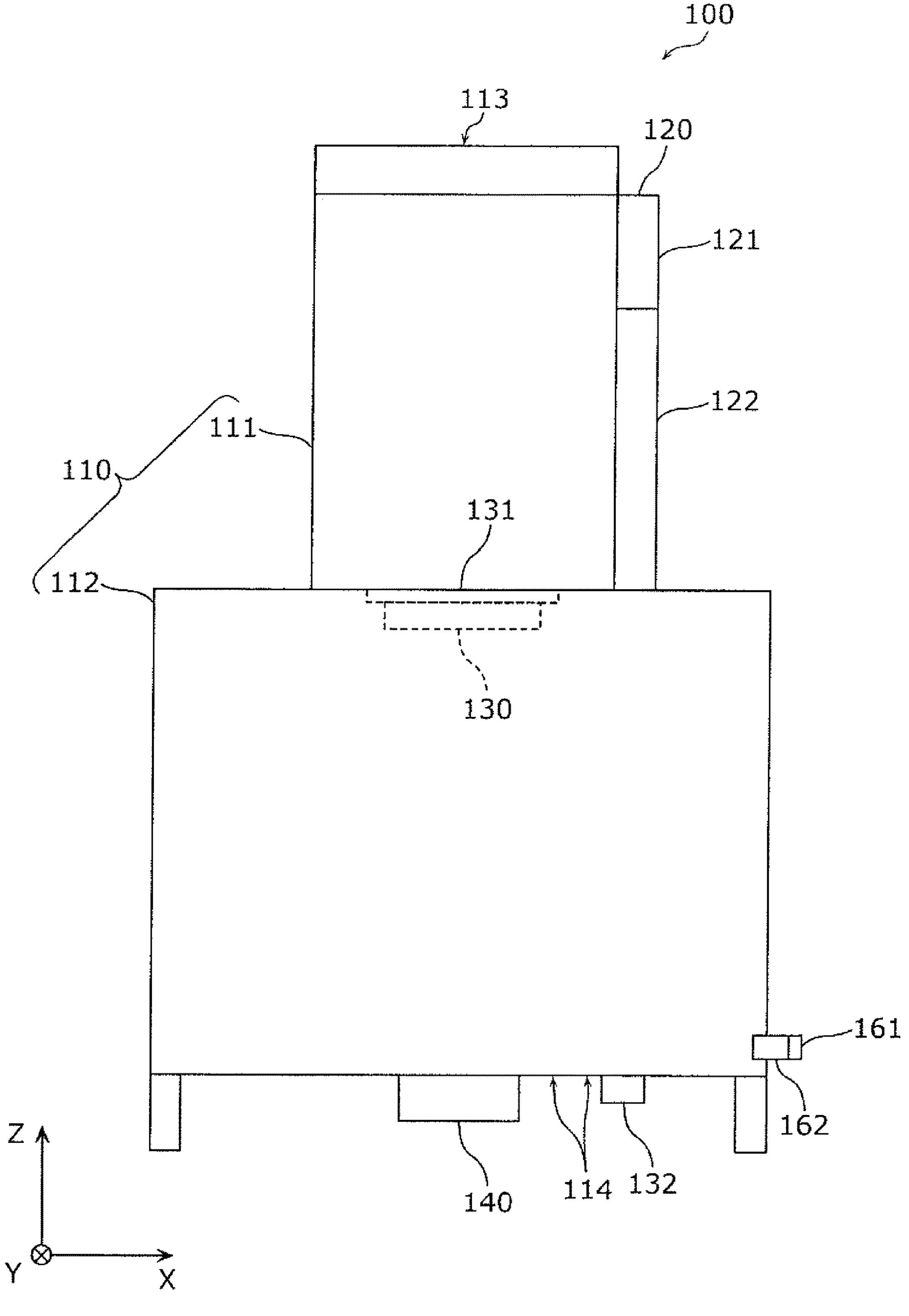
FIG. 2 is a front view of the particulate collection device according to Embodiment 1.
Figure 3:
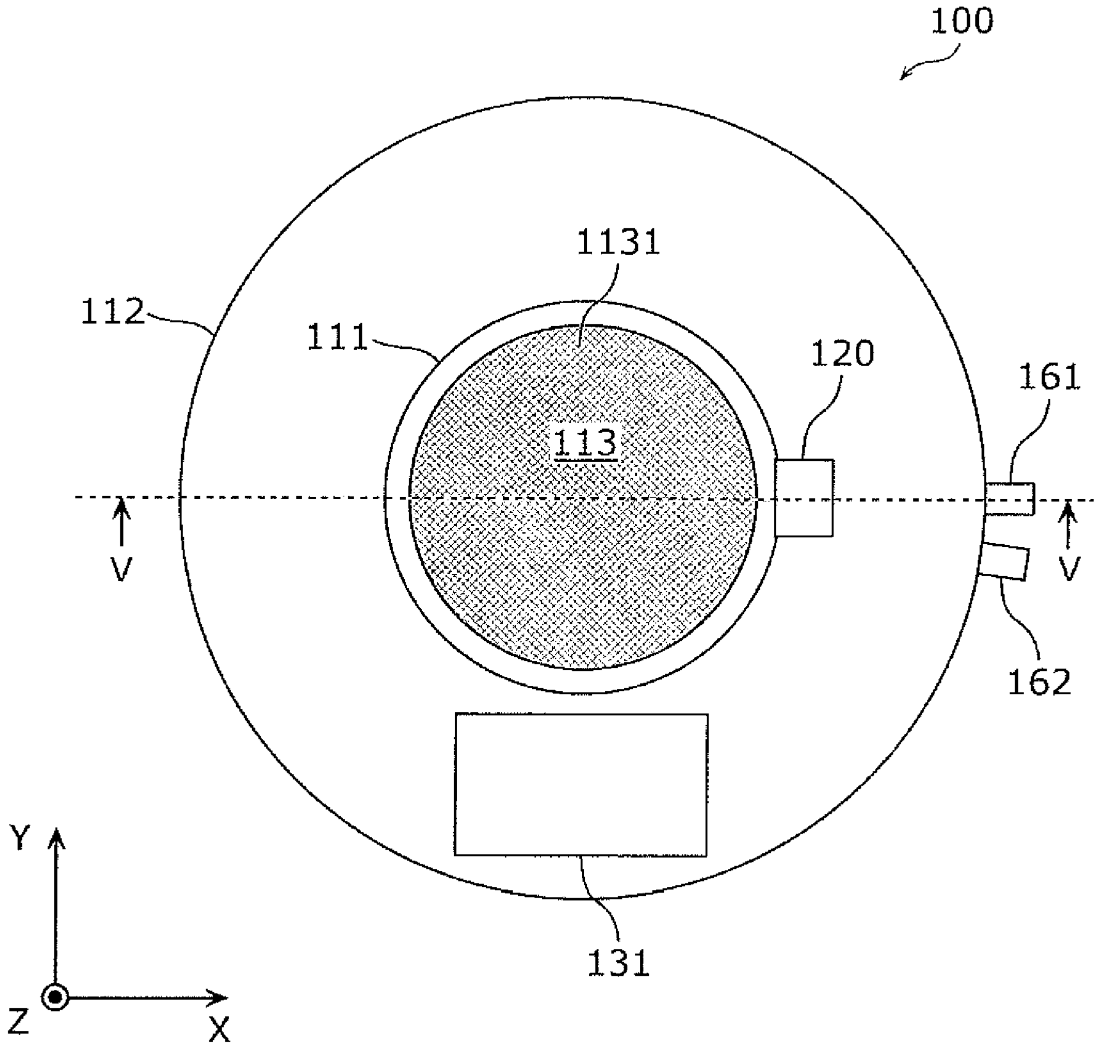
FIG. 3 is a plan view of the particulate collection device according to Embodiment 1.
Figure 4:
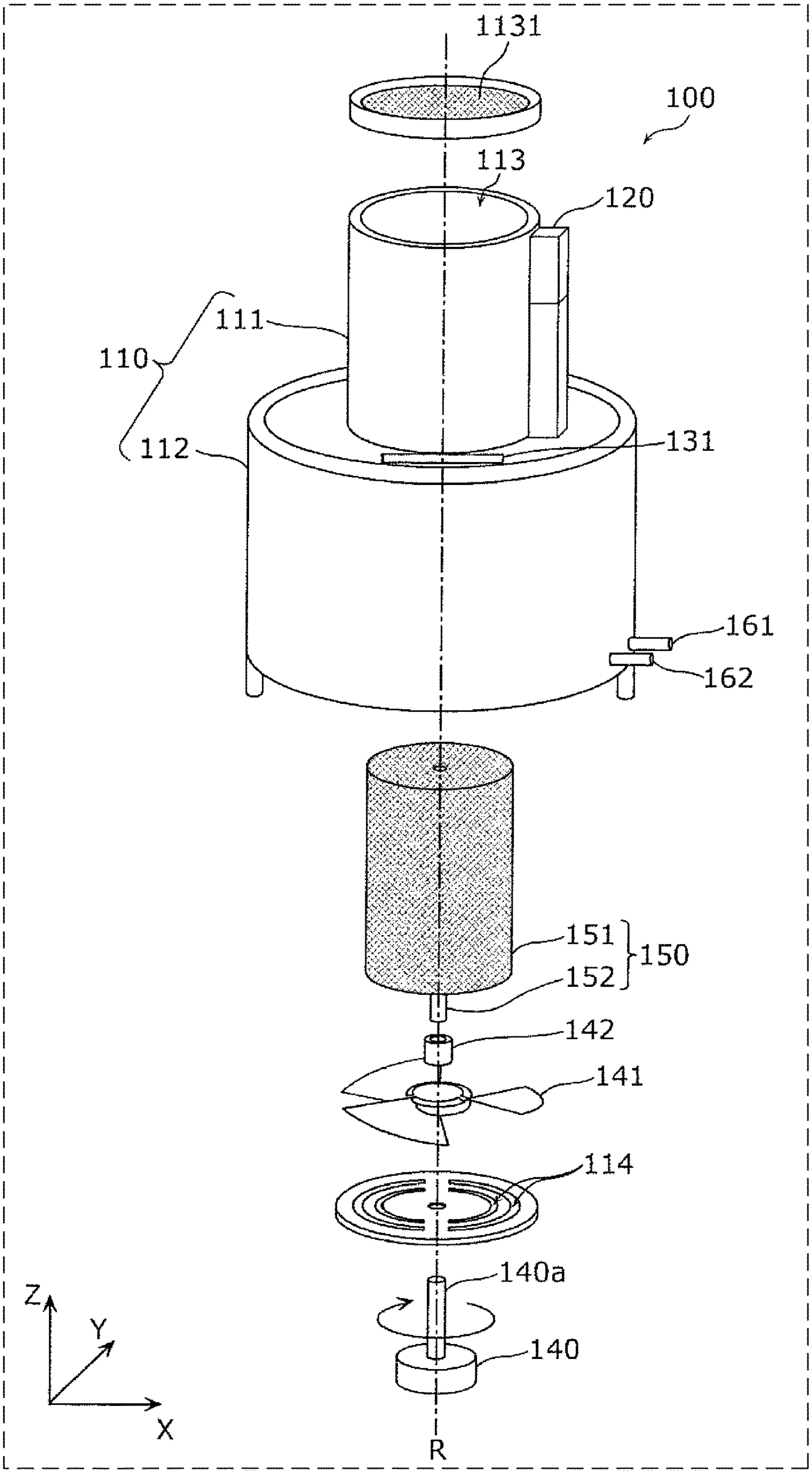
FIG. 4 is an exploded perspective view of the particulate collection device according to Embodiment 1.
Figure 5:
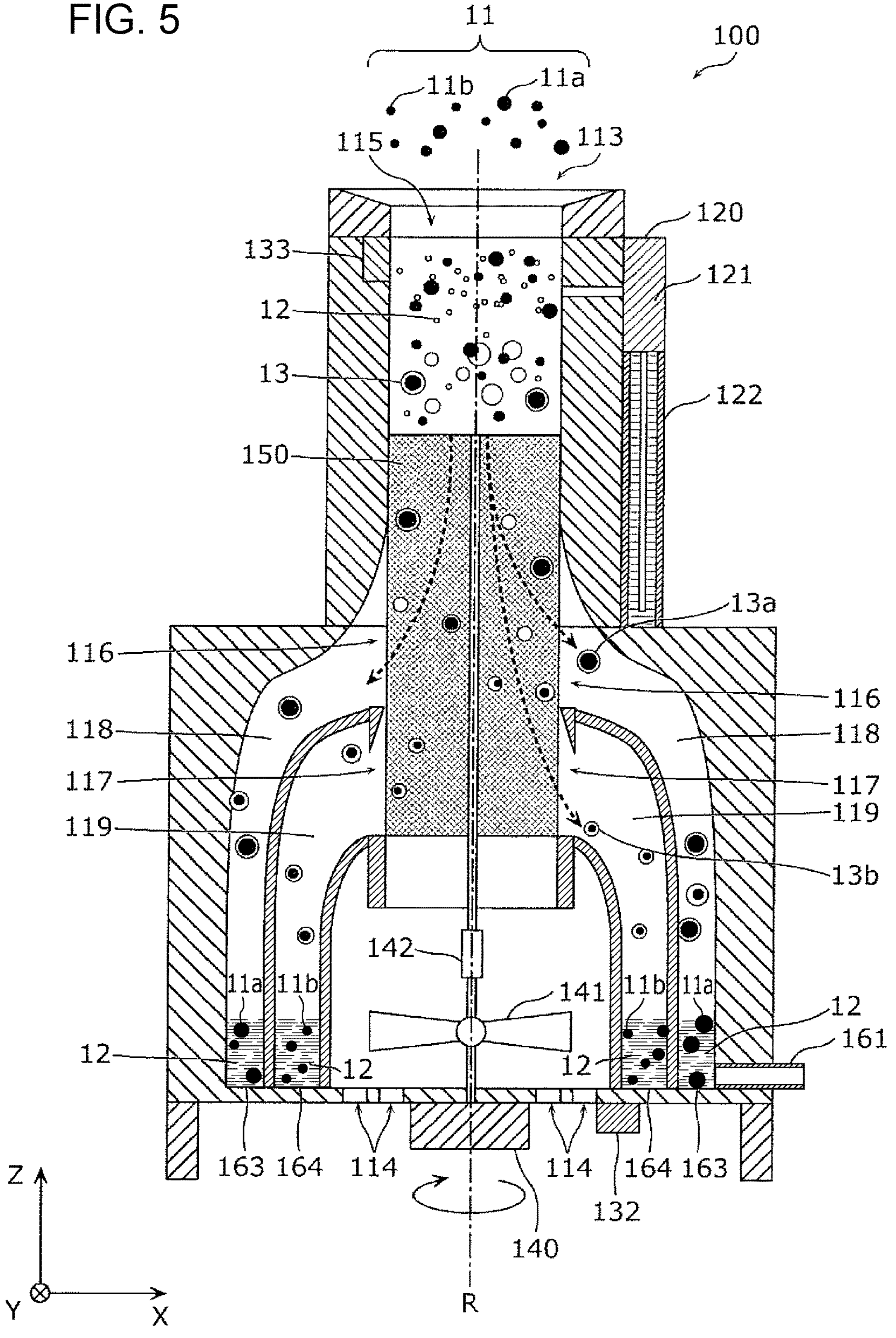
FIG. 5 is a sectional view of the particulate collection device according to Embodiment 1.

The configuration of a particulate collection device 100 is described in detail first with reference to FIGS. 1 to 5. FIG. 1 is a perspective view of the particulate collection device 100 according to Embodiment 1. FIG. 2 is a front view of the particulate collection device 100 according to Embodiment 1. FIG. 3 is a plan view of the particulate collection device 100 according to Embodiment 1. FIG. 4 is an exploded perspective view of the particulate collection device 100 according to Embodiment 1. FIG. 5 is a sectional view of the particulate collection device 100 according to Embodiment 1. More specifically, FIG. 5 is a sectional view taken along line V-V of FIG. 3. Note that in FIG. 5, particulates 11 to be collected, first liquid 12, and a droplet 13, which is a particulate 11 coated by the first liquid 12, are also illustrated.

The particulate collection device 100 collects the particulates 11 from a gas (also called aerosol) containing the particulates 11. At this time, the particulate collection device 100 classifies the particulates 11 into first particulates 11*a* and second particulates 11*b* that are smaller than the first particulates 11*a*. That is, the particulate collection device 100 distinguishes the first particulate 11*a* from the second particulate 11*b*, which differs from the first particulate 11*a* in size, and collects the particulates. The first particulates 11*a* and the second particulates 11*b* collected by the particulate collection device 100 are analyzed separately by an analyzer (not illustrated).

For example, the particulates 11 can contain a target substance. By analyzing the particulates 11, the target substance in the particulates 11 can be detected. An example of a target substance can be an influenza virus. At this time, the first particulate 11*a* may be an airborne droplet (with a particulate diameter of about 5 micrometers) that can contain the influenza virus, and the second particulate 11*b* may be a droplet nucleus (with a particulate diameter of about 0.5 micrometers).

Note that the target substance is not limited to an influenza virus. For example, the target substance may be another virus or a living organism (e.g., a bacteria) other than viruses. The target substance does not have to be a living organism, and may be an environmental pollutant, an allergen, or the like.

As illustrated in FIGS. 1 to 3, the particulate collection device 100 includes a housing 110, a spray unit 120, a control unit 130, an input unit 131, a power source 140, a first discharge port 161, a second discharge port 162, and a first sensor 132. As illustrated in FIGS. 4 and 5, the particulate collection device 100 further includes, inside the housing 110, a second sensor 133, a fan 141, a transmission 142, and a first filter 150. Each of the constituent elements of the particulate collection device 100 is described below.

As illustrated in FIG. 1, the housing 110 is composed of an upper housing 111 having an air intake port 113 and a lower housing 112 having an exhaust port 114. As illustrated in FIG. 5, the housing 110 has, thereinside, a flow channel 115 that connects the air intake port 113 to the exhaust port 114.

The upper housing 111 is the upper portion of the housing 110 and has a cylindrical shape with a diameter smaller than that of the lower housing 112. The lower housing 112 is the lower portion of the housing 110 and has a cylindrical shape with a diameter larger than that of the upper housing 111. Note that the shape of the upper housing 111 and the lower housing 112 is not limited to a cylindrical shape. For example, the shape may be a square cylinder shape.

The air intake port 113 is an opening formed in the upper surface of the upper housing 111 for drawing outside air into the flow channel 115 in the housing 110. As illustrated in FIGS. 1 and 3, a second filter 1131 can be attached to the air intake port 113.

The second filter 1131 is a filter that is removably attached to the housing 110. The second filter 1131 is used to prevent particulates 11 from entering the flow channel 115 during cleaning. The second filter 1131 is attached to the air intake port 113 when cleaning the inside of the housing 110. The second filter 1131 blocks the particulates 11 and particulates larger than the particulates 11.

When collecting particulates 11, instead of attaching the second filter 1131 to the air intake port 113, a third filter (not illustrated) may be attached to prevent particulates larger than the particulates 11, such as dust or dirt, from entering the housing 110. The third filter allows particulates 11 to pass therethrough and blocks particulates larger than the particulates 11.

The exhaust port 114 is an opening formed in the lower surface of the lower housing 112 to discharge gas from the flow channel 115 in the housing 110. The gas that has passed through the first filter 150 is discharged from the exhaust port 114.

The flow channel 115 is formed across the upper housing 111 and lower housing 112 of the housing 110.

The gas drawn through the air intake port 113 passes through the flow channel 115 and is discharged from the exhaust port 114. In FIG. 5, the flow channel 115 extends along the Z-axis, and its flow direction is a negative direction (a downward direction) of the Z-axis.

The second sensor 133 detects, from the gas drawn into the air intake port 113, the concentration of particulates each having a diameter greater than or equal to a predetermined second particulate diameter. For example, a light scattering particle counter or a light blocking particle counter can be used as the second sensor 133. As the second particulate diameter, the lower limit of the particulate diameter of the particulates 11 can be used. A value set by the user may be used as the second particulate diameter.

Note that the second sensor 133 may detect, from the gas drawn into the air intake port 113, the concentration of particulates each having a particulate diameter greater than or equal to the second particulate diameter and less than or equal to a third particulate diameter. If the lower limit of the particulate diameter of the particulates 11 is used as the second particulate diameter and the upper limit of the particulate diameter of the particulates 11 is used as the third particulate diameter, the second sensor 133 can detect the concentration of the particulates 11 in the gas.

In FIG. 5, the second sensor 133 is installed near the air intake port 113 of the flow channel 115. However, the second sensor 133 does not have to be installed near the air intake port 113. For example, the second sensor 133 may be installed near the exhaust port 114. In this case, the second sensor 133 may further function as the first sensor 132. That is, the second sensor 133 may be the first sensor 132.

As illustrated in FIG. 5, the spray unit 120 sprays first liquid 12 into a portion included in the flow channel 115 and between the air intake port 113 and the first filter 150. That is, the spray unit 120 sprays the first liquid 12 in the form of mist toward the gas present in the portion. At this time, each of the first particulates 11*a* and the second particulates 11*b* collides with the first liquid 12 and is coated by the first liquid 12. As a result, a droplet 13 containing the particulate 11 is formed. The droplets 13 include a first droplet 13*a* containing the first particulate 11*a* and a second droplet 13*b* containing the second particulate 11*b*.

It can be said that the first liquid 12 includes the first liquid 12-1 and the first liquid 12-2, the first particulate 11*a* is coated by the first liquid 12-1, and the second particulate 11*b* is coated by the first liquid 12-2.

Liquid for analyzing the first particulates 11*a* and the second particulates 11*b* can be used as the first liquid 12 to be sprayed by the spray unit 120. The term "liquid for analyzing the first particulates 11*a* and the second particulates 11*b*" refers to a liquid used for analysis, a liquid that maintains the activity of the target substance contained in the particulates 11 for analysis, a liquid that imparts a label or the like to the target substance contained in the first particulates 11*a* and the second particulates 11*b* for analysis, a liquid that protects the target substance contained in the particulates 11 for analysis, or any combination thereof. For example, if the target substance is an influenza virus, examples of the first liquid 12 to be used include a liquid intended to dissolve or preserve the target substance, such as normal saline solution, PBS buffer, EDTA buffer, or bicarbonate buffer, or a liquid containing a substance that specifically binds to the virus and emits magnetism or fluorescence. Note that the first liquid 12 does not have to be a liquid for the analysis of the particulates 11. For example, the first liquid 12 can be pure water.

Furthermore, the spray unit 120 can spray a second liquid. Examples of the second liquid sprayed by the spray unit 120 include a cleaning liquid for cleaning the first filter 150 and the flow channel 115 in the housing 110. For example, if a liquid that dissolves the particulates 11 is used as the second liquid, the particulates 11 remaining in the housing 110 can be effectively removed. Note that if cleaning is not needed, the spray unit 120 need not spray the second liquid.

As illustrated in FIG. 5, the spray unit 120 has an atomizer 121 and a tank 122.

The atomizer 121 is connected to the tank 122 and sprays the liquid stored in the tank 122 into the flow channel 115. The method for spraying the liquid by the atomizer 121 is not limited to a particular method.

The tank 122 may store both the first liquid 12 and the second liquid separately. In this case, the atomizer 121 may switch between the first liquid 12 and the second liquid, based on, for example, a control signal received from the control unit 130 or a user operation and spray the liquid. The tank 122 may be replaceable. In this case, the tank 122 may include a tank having the first liquid 12 stored therein and a tank having the second liquid stored therein. The tank having the first liquid 12 stored therein may be replaced as needed, and the tank having the second liquid stored therein may be replaced as needed.

The first filter 150 is disposed downstream of the spray unit 120 in the flow channel 115 and is supported in a rotatable manner about an R-axis parallel to the Z-axis. According to the present embodiment, the first filter 150 includes a cylindrical-shaped filter unit 151 and a shaft 152 that penetrates the filter unit 151. The shaft 152 is connected to the power source 140 via the transmission 142. The filter unit 151 rotates together with the shaft 152. For example, a fiber member or a porous member that enables the particulates 11 to pass therethrough can be used as the filter unit 151.

When the power source 140 rotates the first filter 150, the droplet 13 flowing in the flow channel 115 together with the gas collides with the first filter 150 and receives a force in a direction away from the R-axis. At this time, the droplet 13 having a larger size is more frequently collides with the fibers that make up the filter and, thus, the speed of movement along the R-axis is decreased. In addition, the droplet 13 having a larger size has a greater centrifugal force due to its larger mass and, thus, the speed in the direction away from the R-axis is increased. That is, the droplet 13 having a larger size leaves the first filter 150 at a more upstream point and reaches the wall of the flow channel 115 at a more upstream point. In FIG. 5, the first droplet 13*a* containing the first particulate 11*a* is headed toward a first collection port 116 on the upstream side, and the second droplet 13*b* containing the second particulate 11*b* is headed toward a second collection port 117 on the downstream side.

The first collection port 116 is formed on the wall of the flow channel 115 so as to face the first filter 150 and is used to collect the first particulates 11*a* each coated by the first liquid 12. That is, the first droplet 13*a* is collected at the first collection port 116. According to the present embodiment, the first collection port 116 surrounds the first filter 150 in a belt-like manner. The first collection port can be considered to be a port for collecting the first particulates 11*a* that is coated with the first liquid and that have passed through a portion contained in the first filter 150 from the flow channel 115.

The second collection port 117 is formed on the wall of the flow channel 115 so as to face the first filter 150, downstream of the first collection port 116. The second collection port 117 collects the second particulates 11*b* each coated with the first liquid 12. That is, the second droplet 13*b* is collected at the second collection port 117. According to the present embodiment, the second collection port 117 surrounds the first filter 150 in a belt-like manner. The second collection port can be considered to be a port for collecting the second particulates 11*b* that is coated with the first liquid and that have passed through a portion contained in the first filter 150 from the flow channel 115.

In FIG. 5, the first collection port 116 and the second collection port 117 are adjacent to each other without any spacing along the Z-axis. However, the arrangement is not limited thereto. For example, the first collection port 116 and the second collection port 117 may be disposed along the Z-axis with a spacing therebetween. In addition, the first collection port 116 and the second collection port 117 do not have to completely surround the first filter 150. That is, the shape of each of the first collection port 116 and the second collection port 117 is not limited to a belt-like shape.

A first holding unit 163 holds, in the first liquid 12, the first particulate 11*a* collected at the first collection port 116. In FIG. 5, the first holding unit 163 is provided at the top end of a first duct 118 that communicates with the first collection port 116. The first duct 118 is disposed on the outer side a second duct 119 and extends from the first collection port 116 to the lower part of the lower housing 112. The first droplets 13*a* collected at the first collection port 116 clump together, flow downward in the first duct 118 under their own weight, and reach the first holding unit 163.

A second holding unit 164 holds, in the first liquid 12, the second particulates 11*b* collected at the second collection port 117. In FIG. 5, the second holding unit 164 is provided at the top end of the second duct 119 that communicates the second collection port 117. The second duct 119 surrounds the outer side of the flow channel 115 and extends from the second collection port 117 to the lower part of the lower housing 112. The second droplets 13*b* collected at the second collection port 117 clump together, flow downward in the second duct 119 under their own weight, and reach the second holding unit 164.

Note that the first duct 118 and the second duct 119 may be separate ducts or may be composed by partitioning a single flared duct with a partition. The particulate collection device 100 does not necessarily have to include the first holding unit 163 and the second holding unit 164. In this case, the first collection port 116 and the second collection port 117 may be directly connected to the first discharge port 161 and the second discharge port 162, respectively.

The first discharge port 161 discharges the first particulate 11*a* and the first liquid 12 collected at the first collection port 116 to the outside of the housing 110. More specifically, the first discharge port 161 is connected to the first holding unit 163 and discharges the first particulate 11*a* and the first liquid 12 held in the first holding unit 163.

The second discharge port 162 discharges the second particulate 11*b* and the first liquid 12 collected at the second collection port 117 to the outside of the housing 110. More specifically, the second discharge port 162 is connected to the second holding unit 164 and discharges the second particulate 11*b* and the first liquid 12 held in the second holding unit 164.

Note that the first discharge port 161 and the second discharge port 162 may be connected directly to an analyzer (not illustrated). In this case, the first particulate 11*a* and the first liquid 12 held in the first holding unit 163 are sent to the analyzer via the first discharge port 161, and the second particulate 11*b* and the first liquid 12 held in the second holding unit 164 are sent to the analyzer via the second discharge port 162.

The power source 140 rotates the first filter 150 about the R-axis. In addition, the power source 140 rotates the fan 141 about the R-axis. The power source 140 is controlled by the control unit 130. For example, an electric motor can be used as the power source 140. According to the present embodiment, the power source 140 is mounted on the lower surface of the lower housing 112. However, the mounting position of the power source 140 is not limited thereto.

The fan 141 is a blower that generates airflow in the negative direction of the Z-axis to draw the gas into the flow channel 115 through the air intake port 113 and discharges, from the exhaust port 114, the gas that has passed through the flow channel 115. The fan 141 is connected to a shaft 140*a* extending from the power source 140 and rotates about the R-axis. The shaft that rotates the first filter 150 and the shaft that rotates the fan 141 may be different shafts and may be disposed parallel. Different power sources may be provided to rotate these two shafts.

The transmission 142 is connected between the fan 141 and the first filter 150 and changes the rotational speed of the shaft 140*a* that extends from the power source 140. For example, the transmission 142 can switch between gear ratios. The selection of the gear ratio may be performed by the control unit 130 described below.

The first sensor 132 detects, in the gas output from the exhaust port 114, a particulate having a particulate diameter greater than or equal to a predetermined first particulate diameter. For example, a light scattering particle counter or a light blocking particle counter can be used as the first sensor 132. As the first particulate diameter, for example, the lower limit of the particulate diameter of the particulates 11 can be used. In this case, the first sensor 132 detects the particulate 11 that has not been collected by the particulate collection device 100. In FIGS. 2 and 5, the first sensor 132 is installed near the exhaust port 114 on the lower surface of the lower housing 112.

The control unit 130 controls the rotational speed of the first filter 150 by controlling the power source 140. According to the present embodiment, the control unit 130 controls the rotational speeds of the first filter 150 and the fan 141 by controlling the power source 140 and the transmission 142.

More specifically, the control unit 130 controls the rotational speed of the first filter 150 on the basis of the input from the user to the input unit 131. Furthermore, the control unit 130 controls the rotational speed of the first filter 150 on the basis of an output signal output from the first sensor 132. Note that the control performed by the control unit 130 is described in detail below with reference to a flowchart illustrated in FIG. 6.

In FIG. 3, the control unit 130 is located below the input unit 131. However, the location of the control unit 130 is not limited thereto.

The input unit 131 receives, from a user, input information on the size of the first particulate 11*a* and the second particulate 11*b*. An example of the size information is a boundary size (e.g., a particulate diameter) of each of the first particulate 11*a* and the second particulate 11*b*. Alternatively, information for identifying the types of the first particulate 11*a* and the second particulate 11*b* (e.g., a droplet or a droplet nucleus) may be used as the size information. Note that the input unit 131 may further receive, from the user, an input of information on the wind speed in the flow channel 115.

According to the present embodiment, a touch display is employed as the input unit 131. However, the input unit 131 is not limited thereto. For example, the input unit 131 may be a mechanical button or a mechanical dial.

Note that the input unit 131 does not necessarily have to be included in the particulate collection device 100. For example, an input from the user may be received by an information terminal (e.g., a smartphone or a tablet). In this case, the particulate collection device 100 may include a communication unit for receiving information on the sizes of the first particulate 11*a* and the second particulate 11*b* from the information terminal.

Operation Performed by Particulate Collection Device

Figure 6:
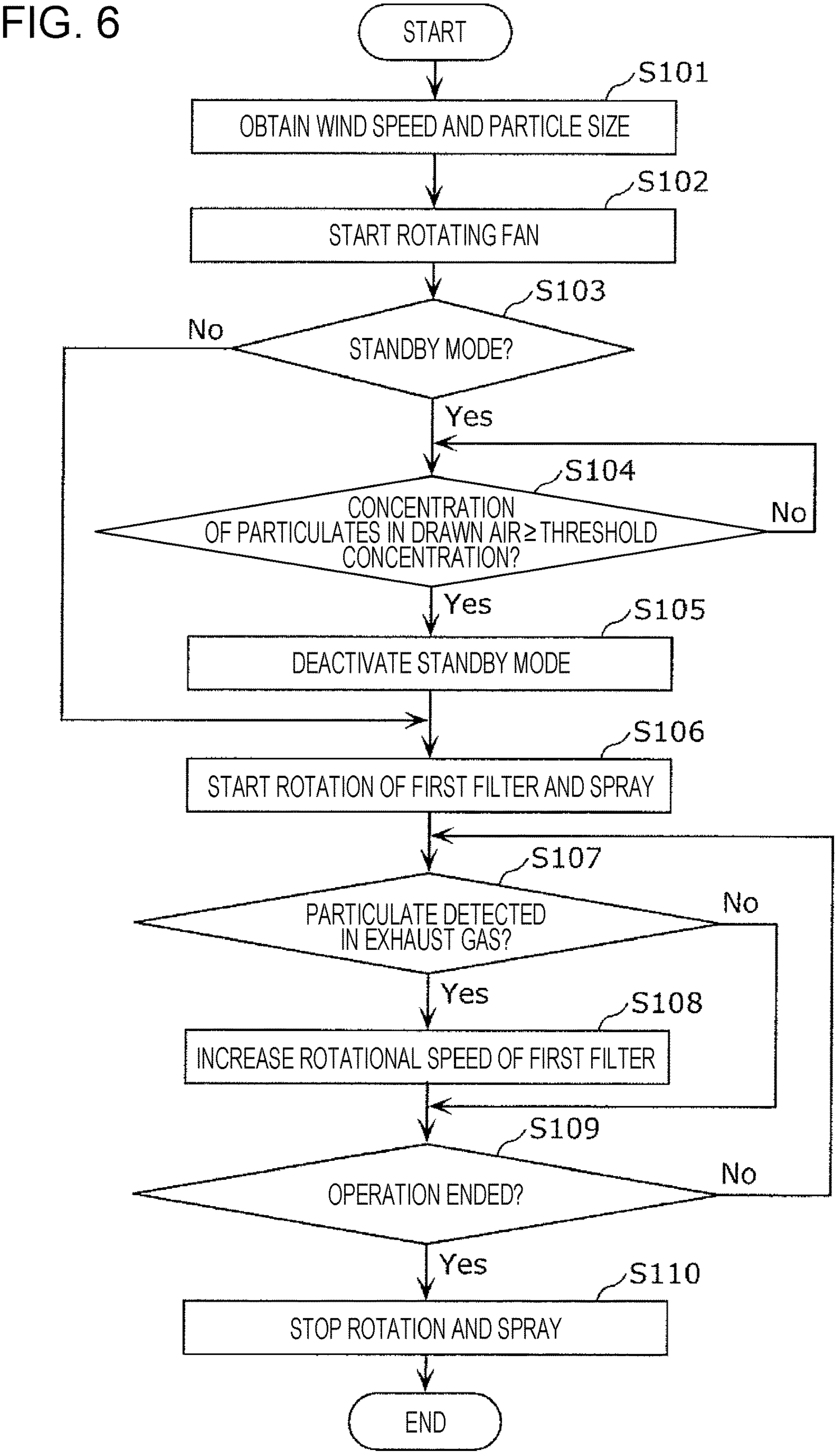
FIG. 6 is a flowchart illustrating the operation performed by the particulate collection device according to Embodiment 1.

The operation performed by the particulate collection device 100 having the configuration described above is described below in detail with reference to FIG. 6. FIG. 6 is a flowchart illustrating the operation performed by the particulate collection device 100 according to Embodiment 1.

The control unit 130 obtains the wind speed and the particulate diameters from the user via the input unit 131 first (S101). Subsequently, the control unit 130 starts rotating the fan 141 on the basis of the obtained wind speed and particulate diameters (S102). For example, the control unit 130 rotates the fan 141 by rotating the power source 140 at a rotational speed corresponding to the obtained wind speed. At this time, the control unit 130 does not rotate the first filter 150 by disconnecting the transmission 142.

At this time, the control unit 130 determines whether a standby mode is set (S103). The standby mode is a mode for waiting for collection of the particulates 11 until gas containing the particulates 11 is drawn. More specifically, in the standby mode, the rotation of the first filter 150 and the spraying by the spray unit 120 are stopped, and the fan 141 is rotated.

At this time, if the standby mode is not set (No in S103), the control unit 130 skips the subsequent steps S104 and S105. However, if the standby mode is set (Yes in S103), the control unit 130 determines whether the concentration of the particulates detected by the second sensor 133 is greater than or equal to a threshold concentration (S104). An example of the threshold concentration is a concentration predetermined empirically or experimentally.

If the detected concentration of the particulates is less than the threshold concentration (No in S104), step S104 is repeated. However, if the concentration of the detected particulates is greater than or equal to the threshold concentration (Yes in S104), the control unit 130 deactivates the standby mode (S105). At this time, the control unit 130 may record the date and time or the time when the standby mode is deactivated. The recorded date and time or time may be available for reference by the user via, for example, the input unit 131.

Subsequently, the control unit 130 starts rotating the first filter 150 and spraying by the spray unit 120 (S106). More specifically, the control unit 130 rotates the first filter 150 at a rotational speed corresponding to the wind speed and particulate diameters obtained in step S101 by controlling the transmission 142. Furthermore, the control unit 130 causes the spray unit 120 to spray the first liquid 12.

The control unit 130 determines whether the first sensor 132 has detected particulates in the exhaust gas (S107). If the first sensor 132 has detected a particulate (Yes in S107), the control unit 130 increases the rotational speed of the first filter 150 (S108). However, if the first sensor 132 has not detected a particulate (No in S107), the control unit 130 skips step S108 and keeps the rotational speed of the first filter 150 unchanged.

Subsequently, the control unit 130 determines whether to end the operation performed by the particulate collection device 100 (S109). For example, the control unit 130 may determine that the operation is to be ended when a predetermined time has elapsed since the deactivation of the standby mode. If it is determined that the operation is not to be ended (No in S109), the processing returns to step S107.

If it is determined that the operation is to be ended (Yes in S109), the control unit 130 stops rotating the fan 141 and the first filter 150 and stops spraying by the spray unit 120 (S110). Thus, the control unit 130 ends the processing.

Effects

As described above, according to the present embodiment, the particulate collection device 100 includes the housing 110 having the air intake port 113 and the exhaust port 114 and the flow channel 115 connecting the air intake port 113 to the exhaust port 114 thereinside, the fan 141 that generates, in the flow channel 115, airflow for drawing, from the air intake port 113 into the flow channel 115, gas containing the first particulate 11*a* and the second particulate 11*b* smaller than the first particulate 11*a* and that is rotatable about the R-axis, the spray unit 120 that sprays the first liquid 12 into a first portion included in the flow channel 115 to coat the first particulate 11*a* with liquid contained in the first liquid and coat the second particulate 11*b* with the liquid contained in the first liquid, the first filter 150 located between the first portion and the exhaust port 114 and supported rotatably about the R-axis, a power source 140 that rotates the first filter 150, the first collection port 116 used to collect the first particulate 11*a* coated with the liquid contained in the first liquid 12 from the flow channel 115 through a second portion in the first filter 150, and the second collection port 117 used to collect the second particulate 11*b* coated with the liquid contained in the first liquid 12 from the flow channel 115 through a third portion included in the first filter 150, where the second portion can be between the first and third portions. The second portion can be located between the first portion and the third portion.

According to the configuration, the first particulate 11*a* and the second particulate 11*b* can be coated with the first liquid 12 by the spray unit 120, and the first filter 150 can collect the first particulate 11*a* and the second particulate 11*b*. Therefore, the particulate collection device 100 need not include all of the heating unit, heating humidification unit, cooling humidification unit, cooling unit, and reheating unit. Thus, size reduction of the device, energy saving, and faster collection can be achieved.

In addition, according to the configuration, the particulate collection device 100 can collect the first particulate 11*a* and the second particulate 11*b* by rotating the first filter 150. As a result, the particulate collection device 100 can reduce pressure loss more than separation based on inertial collision and, thus, energy saving can be achieved. Furthermore, the particulate collection device 100 can reduce the device size or pressure loss more than filtration using a stationary membrane filter, thus achieving size reduction or energy saving. In addition, clogging of the first filter 150 can be prevented, and the frequency of cleaning and replacement of the filter can be reduced.

In addition, according to the configuration, the particulate collection device 100 can collect the first particulate 11*a* and the second particulate 11*b* separately at the first collection port 116 and the second collection port 117, respectively. Therefore, the first particulate 11*a* and the second particulate 11*b* can be separately analyzed easily and, thus, the accuracy of analysis can be improved.

In addition, according to the configuration, the particulate collection device 100 can coat the first particulate 11*a* and the second particulate 11*b* with the first liquid 12 by using the spray unit 120. As a result, due to an increase in the particulate diameter of each of the first particulate 11*a* and the second particulate 11*b*, the efficiency of collection by the filter can be improved. Furthermore, drying of the first particulate 11*a* and the second particulate 11*b* can be prevented, which can protect a living body when, for example, the target substance contained in the first particulate 11*a* and the second particulate 11*b* is the living body. As a result, the target substance can be detected effectively, and the accuracy of analysis of the first particulate 11*a* and second particulate 11*b* can be improved. Still furthermore, the first particulate 11*a* and the second particulate 11*b* can be coated with the first liquid 12 by spraying, and the first particulate 11*a* and the second particulate 11*b* can be collected in the first liquid 12 at a high concentration while reducing the amount of the first liquid 12 used. As a result, the accuracy of analysis of the first particulate 11*a* and the second particulate 11*b* can be improved, and the time required for analysis can be reduced.

According to the present embodiment, the particulate collection device 100 can further include the first discharge port 161 used to discharge, to the outside of the housing 110, the first particulate 11*a* and the liquid contained in the first liquid 12 and coating the first particulate, which are collected at the first collection port 116, and a second discharge port 162 used to discharge, to the outside of the housing 110, the second particulate 11*b* and liquid contained in the first liquid 12 and coating the second particulate, which are collected at the second collection port 117.

According to the configuration, the first particulate 11*a* and the second particulate 11*b* can be discharged separately from the first discharge port 161 and the second discharge port 162, respectively. For example, if the first discharge port 161 and the second discharge port 162 are connected to an analyzer, the collected first particulates 11*a* and second particulates 11*b* can be analyzed in real time.

In the particulate collection device 100 according to the present embodiment, the first liquid can be a liquid used to analyze the first particulate 11*a* and the second particulate 11*b*.

According to the configuration, the first particulate 11*a* and the second particulate 11*b* can be collected together with the first liquid 12 for analysis of the first particulate 11*a* and the second particulate 11*b* and, thus, the efficiency of the analysis of the first particulate 11*a* and the second particulate 11*b* and/or the accuracy of the analysis and the like can be increased. For example, if the first liquid 12 is a liquid used for analysis, the process of causing the first liquid 12 to act on the first particulate 11*a* and the second particulate 11*b* during analysis can be removed and, thus, the efficiency of analysis can be increased. In addition, if the first liquid 12 is a liquid for maintaining the activity of the living organism contained in the first particulate 11*a* and the second particulate 11*b*, the first particulate 11*a* and the second particulate 11*b* can be collected with the activity of the living organism being maintained and, thus, the accuracy of analysis can be increased.

In addition, the particulate collection device 100 according to the present embodiment can further include the second filter 1131 removably attached to the air intake port 113 and preventing the first particulate 11*a* and the second particulate 11*b* from entering the flow channel 115. The spray unit 120 can spray a second liquid to clean the first filter 150 and the flow channel 115 when the second filter 1131 is attached.

According to the configuration, the particulate collection device 100 can clean the first filter 150 and the flow channel 115 by changing the liquid to be sprayed. Thus, the first particulate 11*a* and second particulate 11*b* remaining in the first filter 150 can be removed, and clogging of the first filter 150 during continuous use can be prevented. In addition, contamination can be prevented when long-term and multiple collections and multiple analysis attempts are performed at different points in time.

In addition, according to the configuration, since during cleaning, the particulate collection device 100 can prevent new first particulate 11*a* and second particulate 11*b* from entering the flow channel 115 by using the second filter 1131, the particulate collection device 100 can efficiently clean the first filter 150 and the flow channel 115.

In addition, the particulate collection device 100 according to the present embodiment can further include a control unit 130 that controls the rotational speed of the first filter 150.

According to the configuration, since the particulate collection device 100 can change the rotational speed of the first filter 150, the particulate collection device 100 can collect the particulates 11 and classify the particulates 11 in accordance with the sizes of the particulates 11 and the velocity of the airflow in the flow channel 115. Thus, the efficiency for collecting the particulates 11 can be increased.

In addition, the particulate collection device 100 according to the present embodiment can further include the input unit 131 that receives information on the sizes of the first particulate 11*a* and the second particulate 11*b* input by a user, and the control unit 130 can control, based on the input information, the rotational speed of the first filter 150.

According to the configuration, the rotational speed of the first filter 150 can be controlled in accordance with the sizes of the first particulate 11*a* and the second particulate 11*b* and, thus, the particulates 11 contained in the gas can be classified more accurately into the first particulate 11*a* and the second particulate 11*b*. Furthermore, the user can optionally input information on the sizes of the first particulate 11*a* and the second particulate 11*b* via the input unit 131 and, thus, the particulate collection device 100 can improve the convenience for the user.

In addition, the particulate collection device 100 according to the present embodiment can further include the first sensor 132 that detects a particulate having a particulate size greater than or equal to a predetermined first particulate size in a gas output from the exhaust port 114, and the control unit 130 can increase the rotational speed of the first filter 150 if the first sensor 132 detects the particulate.

According to the configuration, if the first sensor 132 detects a particulate, the particulate collection device 100 can increase the rotational speed of the first filter 150 to prevent the particulate from passing through the first filter 150. Thus, the particulate collection device 100 can reduce the number of uncollected first particulates 11*a* and second particulates 11*b*.

In addition, the particulate collection device 100 according to the present embodiment can include the second sensor 133 that detects the concentration of particulates each having a particulate size greater than or equal to a predetermined second particulate size in a gas drawn into the air intake port 113. The control unit can have a standby mode in which rotation of the first filter 150 and spraying performed by the spray unit 120 are stopped and the fan 141 is rotated. If, in the standby mode, the concentration of the particulates detected by the second sensor 133 is higher than or equal to a threshold concentration, the control unit 130 can deactivate the standby mode to start rotation of the first filter 150 and spraying performed by the spray unit 120.

According to the configuration, if the concentration of particulates in the gas is low, the standby mode can avoid unnecessary consumption of the first liquid 12 and energy. For example, if the first particulate 11*a* and the second particulate 11*b* are generated by either human action or natural phenomena, collection performed by the particulate collection device 100 can be started at the same time as the particulates are generated.

Embodiment 2

Embodiment 2 is described below. The present embodiment mainly differs from Embodiment 1 described above in that a particulate collection device includes a humidification unit and a cooling unit instead of including the spray unit. The present embodiment is described below with reference to FIGS. 7 and 8, focusing on the points that differ from Embodiment 1 described above.

Configuration of Particulate Collection Device

Figure 7:
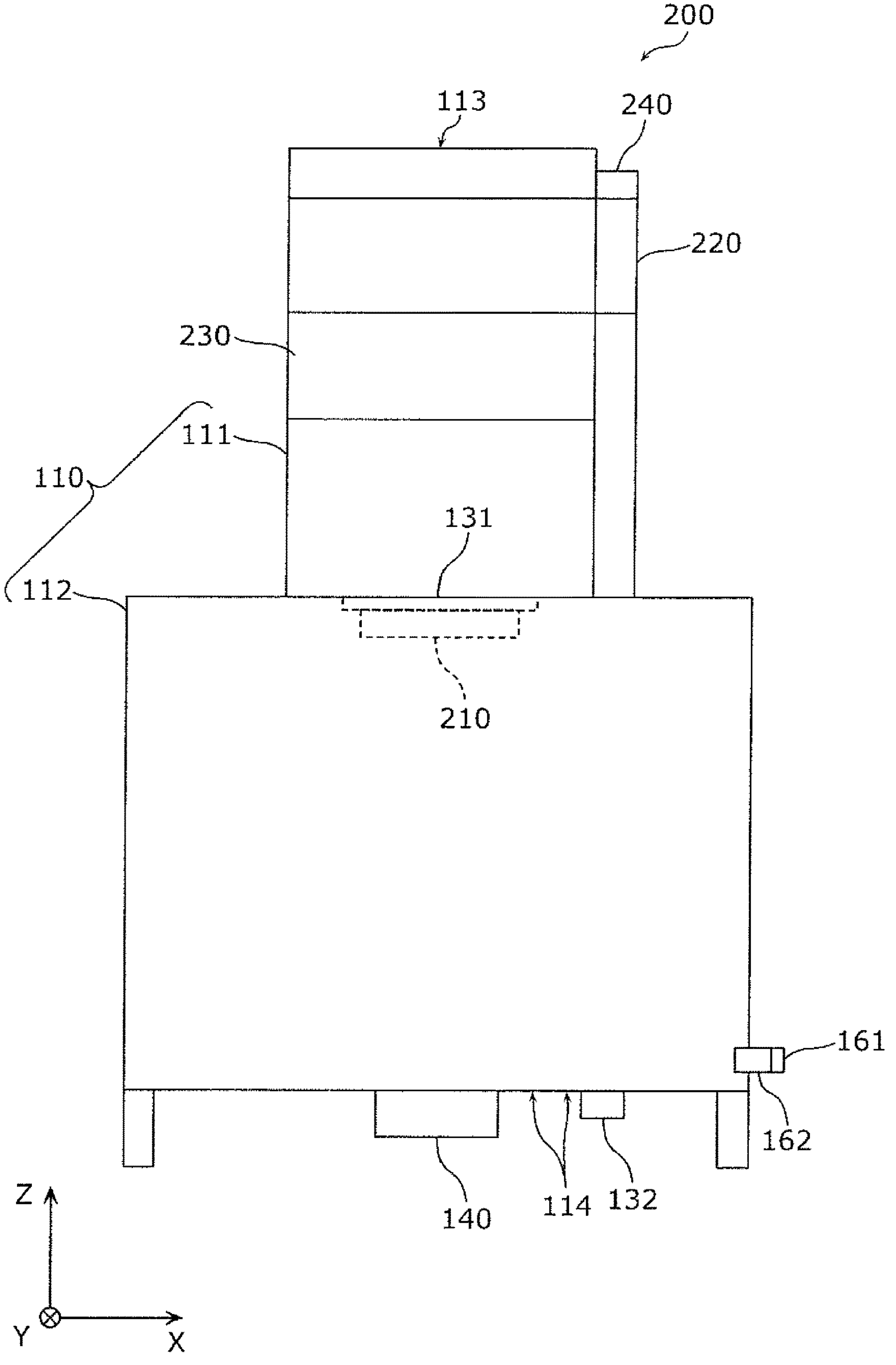
FIG. 7 illustrates a front view of a particulate collection device according to Embodiment 2.
Figure 8:
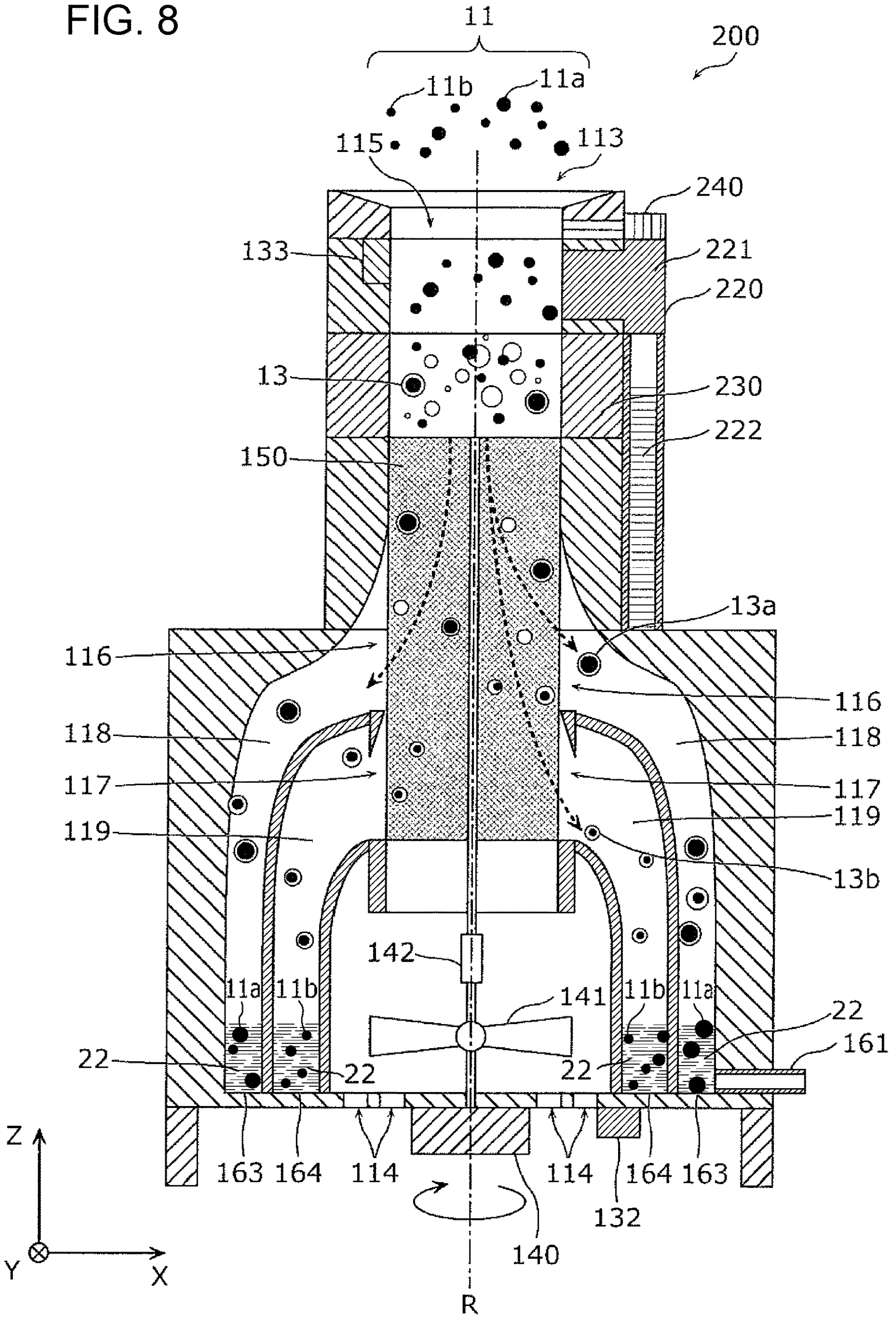
FIG. 8 illustrates a sectional view of the particulate collection device according to Embodiment 2.

FIG. 7 is a front view of a particulate collection device 200 according to Embodiment 2. FIG. 8 is a sectional view of the particulate collection device 200 according to Embodiment 2. The particulate collection device 200 according to the present embodiment includes a control unit 210 instead of the control unit 130 and includes a humidification unit 220 and a cooling unit 230 instead of the spray unit 120. That is, according to the present embodiment, instead of spraying performed by the spray unit 120, humidification by the humidification unit 220 and cooling by the cooling unit 230 are performed. Furthermore, the particulate collection device 200 includes a humidity sensor 240.

The control unit 210 controls at least one of the rotational speed of the first filter 150 or the cooling amount of the cooling unit 230. For example, the control unit 210 may control at least one of the rotational speed of the first filter 150 or the cooling amount of the cooling unit 230 on the basis of information about the sizes of the first particulate 11*a* and the second particulate 11*b* received from the input unit 131. Alternatively, for example, the control unit 210 may increase at least one of the rotational speed of the first filter 150 or the cooling amount of the cooling unit 230 when the first sensor 132 provided at the exhaust port 114 detects a particulate. In addition, for example, the control unit 210 may have a standby mode in which the rotation of the first filter 150, the humidification by the humidification unit 220, and the cooling by the cooling unit 230 are stopped and, in addition, the fan 141 is rotated. In this case, if in the standby mode, the concentration of the particulates detected by the second sensor 133 is greater than or equal to a threshold concentration, the control unit 210 may deactivate the standby mode and start rotation of the first filter 150, humidification by the humidification unit 220, and cooling by the cooling unit 230.

The humidification unit 220 humidifies the gas in the flow channel 115. The humidification unit 220 may adjust the humidification amount on the basis of the humidity level measured by the humidity sensor 240 (described below). For example, the humidification unit 220 may increase the humidifying amount with decreasing measured humidity level.

The humidification unit 220 may humidify the gas in a region included in a first portion included in the flow channel 115. The first portion may be part of the flow channel 115, and the range of the coordinate in the Z-axis of the humidifier 221 may be the same as the range of the coordinate in the Z-axis of the first portion.

In FIG. 8, the humidification unit 220 includes a humidifier 221 and a tank 222 that stores liquid 22 (e.g., water). The humidifier 221 is connected to the tank 222 and humidifies a gas using the liquid 22 stored in the tank 222. Note that the technique for humidifying the gas by the humidifier 221 is not limited to a particular technique.

The cooling unit 230 is located downstream of the humidification unit 220. The cooling unit 230 cools the gas humidified by the humidification unit 220. The technique of cooling the gas by the cooling unit 230 is not limited to a particular technique. For example, the gas can be cooled by heat exchange with cold water.

The cooling unit 230 may cool the gas humidified by the humidification unit 220 in a region included in a second portion included in the flow channel 115. The second portion may be a part of the flow channel 115, and the range of the coordinate in the Z-axis of the cooling unit 230 may be the same as the range of the coordinate in the Z-axis of the second portion.

The humidity sensor 240 is located upstream of the humidification unit 220 and measures the humidity level of the gas drawn through the air intake port 113. The information on the measured humidity level is sent, for example, to the control unit 130 and/or the humidification unit 220. Note that the technique of measuring the humidity level by the humidity sensor 240 is not limited to a particular technique.

As illustrated in FIG. 8, when the gas humidified by the humidification unit 220 is cooled by the cooling unit 230, droplets 13 are formed in the same manner as in Embodiment 1 on the basis of the principle of nuclear condensation. Thereafter, as in Embodiment 1, the droplets 13 are classified by the first filter 150 into the first droplet 13*a* containing the first particulate 11*a* and the second droplet 13*b* containing the second particulate 11*b*.

Effects

As described above, the particulate collection device 200 according to the present embodiment includes the housing 110 having the air intake port 113 and the exhaust port 114 and the flow channel 115 connecting the air intake port 113 to the exhaust port 114 thereinside, the fan 141 that generates, in the flow channel 115, airflow for drawing, from the air intake port 113 into the flow channel 115, a gas containing a first particulate 11*a* and a second particulate 11*b* smaller than the first particulate 11*a*, where the fan is rotatable about the R-axis, the humidification unit 220 that humidifies the gas in a region included in the first portion included in the flow channel 115, the cooling unit 230 that cools, in a region included in the second portion included in the flow channel 115, the gas humidified by the humidification unit 220, coats the first particulate 11*a* with the liquid 22, and coats the second particulate 11*b* with the liquid 22, a first filter 150 located between the second portion and the exhaust port 114 and supported rotatably about the R-axis, the power source 140 that rotates the first filter 150, the first collection port 116 used to collect the first particulate 11*a* coated with the liquid 22 from the flow channel 115 through a third portion included in the first filter 150, and a second collection port 117 used to collect the second particulate 11*b* coated with the liquid 22 from the flow channel 115 through a fourth portion included in the first filter 150. The first portion can be located between the air intake port 113 and the second portion, and the third portion can be located between the second portion and the fourth portion.

According to the configuration, the first particulate 11*a* and the second particulate 11*b* can be coated with the liquid 22 by the humidification unit 220 and the cooling unit 230. Therefore, the first particulate 11*a* and the second particulate 11*b* can be collected by the first filter 150. As a result, the particulate collection device 100 need not include all of the heating unit, heating humidifying unit, cooling humidifying unit, cooling unit, and reheating unit. Thus, size reduction of the device, energy saving, and faster collection can be achieved.

In addition, according to the configuration, the particulate collection device 200 can collect the first particulate 11*a* and the second particulate 11*b* by rotating the first filter 150. Therefore, the particulate collection device 200 can reduce pressure loss more than separation based on inertial collision, and energy saving can be achieved. Furthermore, the particulate collection device 200 can reduce the size of the device or pressure loss more than filtration using a filter and can achieve size reduction or energy saving. Still furthermore, clogging of the first filter 150 can be prevented, and the frequency of cleaning and replacement of the filter can be reduced.

In addition, according to the configuration, the particulate collection device 200 can collect the first particulate 11*a* and the second particulate 11*b* separately at the first collection port 116 and the second collection port 117, respectively. Therefore, the particulate collection device 200 can easily analyze the first particulate 11*a* and the second particulate 11*b* separately, thus increasing the accuracy of analysis.

In addition, according to the configuration, the particulate collection device 200 can coat the first particulate 11*a* and the second particulate 11*b* with the liquid 22 by using the humidification unit 220 and the cooling unit 230. As a result, due to an increase in the particulate diameter of each of the first particulate 11*a* and the second particulate 11*b*, the efficiency of collection by the filter can be improved. Furthermore, drying of the particulates can be prevented, which can protect the living body when, for example, the target substance contained in the first particulate 11*a* and the second particulate 11*b* is a living body. As a result, the target substance can be detected effectively, and the accuracy of analysis of the first particulate 11*a* and second particulate 11*b* can be improved. Still furthermore, the first particulate 11*a* and the second particulate 11*b* can be coated with the liquid 22 through humidification and cooling, and the first particulate 11*a* and the second particulate 11*b* can be collected in the liquid 22 at a high concentration while reducing the amount of the liquid 22 used. As a result, the accuracy of analysis of the first particulate 11*a* and the second particulate 11*b* can be improved, and the time required for analysis can be reduced.

In addition, the particulate collection device 200 according to the present embodiment can further include a first discharge port 161 used to discharge, to the outside of the housing 110, the first particulate 11*a* and the liquid 22 that coats the first particulate 11*a*, which are collected at the first collection port 116, and a second discharge port 162 used to discharge, to the outside of the housing 110, the second particulate 11*b* and the liquid 22 that coats the second particulate 11*b*, which are collected at the second collection port 117.

According to the configuration, the first particulate 11*a* and the second particulate 11*b* can be discharged separately from the first discharge port 161 and the second discharge port 162, respectively. For example, if the first discharge port 161 and the second discharge port 162 are connected to an analyzer, the collected first particulate 11*a* and second particulate 11*b* can be analyzed in real time.

In addition, the particulate collection device 200 can further include a control unit 210 that controls at least one of the rotational speed of the first filter 150 or the cooling amount of the cooling unit 230.

According to the configuration, since the particulate collection device 200 can change the rotational speed of the first filter 150 and/or the cooling amount of the cooling unit 230, the particulate collection device 200 can collect and classify the particulates 11 on the basis of the sizes of the particulates 11 and the velocity of the airflow in the flow channel 115. Thus, the collection efficiency of the particulates 11 can be increased.

In addition, according to the present embodiment, the particulate collection device 200 can further include an input unit 131 that receives information on the sizes of the first particulate 11*a* and the second particulate 11*b* input by a user. The control unit 210 can control, based on the input information, at least one of the rotational speed of the first filter 150 or the cooling amount of the cooling unit 230.

According to the configuration, the rotational speed of the first filter 150 and/or the cooling amount of the cooling unit 230 can be controlled in accordance with the sizes of the first particulate 11*a* and the second particulate 11*b*, and the particulates 11 contained in the gas can be classified into the first particulate 11*a* and the second particulate 11*b* more accurately. Furthermore, the user can optionally input information on the sizes of the first particulate 11*a* and the second particulate 11*b* via the input unit 131. Thus, the particulate collection device 200 can improve the convenience for the user.

In addition, the particulate collection device 200 according to the present embodiment can further include the first sensor 132 that detects a particulate having a particulate size greater than or equal to a predetermined first particulate size in a gas discharged from the exhaust port 114. The control unit 210 can increase at least one of the rotational speed of the first filter 150 or the cooling amount of the cooling unit 230 if the first sensor 132 detects the particulate.

According to the configuration, when the first sensor 132 detects a particulate, the particulate collection device 100 can increase the rotational speed of the first filter 150 and/or the cooling amount of the cooling unit 230 so as to increase the size of the droplet 13. In this manner, the particulate collection device 100 can prevent the particulates 11 from passing through the first filter 150. As a result, the particulate collection device 100 can reduce the number of uncollected first particulates 11*a* and second particulates 11*b*.

In addition, the particulate collection device 200 according to the present embodiment can further include a second sensor 133 that detects the concentration of particulates each having a particulate size greater than or equal to a predetermined second particulate size in a gas drawn into the air intake port 113. The control unit 210 can have a standby mode in which rotation of the first filter 150, humidification performed by the humidification unit 220, and cooling performed by the cooling unit 230 are stopped and the fan 141 is rotated. If, in the standby mode, the concentration of the particulates detected by the second sensor 133 is higher than or equal to a threshold concentration, the control unit 210 can deactivate the standby mode and start rotation of the first filter 150, humidification performed by the humidification unit 220, and cooling performed by the cooling unit 230.

According to the configuration, when the concentration of particulates in the gas is low, the standby mode can prevent unnecessary energy consumption. For example, if the first particulate 11*a* and the second particulate 11*b* are generated by either human action or natural phenomena, collection performed by the particulate collection device 100 can be started at the same time as the particulates are generated.

In addition, the particulate collection device 200 according to the present embodiment can further include a humidity sensor 240 that is disposed upstream of the humidification unit 220 and that measures the humidity of the gas drawn through the air intake port 113, and the humidification unit 220 can control the amount of humidification, based on the humidity measured by the humidity sensor 240.

According to the configuration, the particulate collection device 200 can increase the amount of humidification with decreasing humidity level of the gas drawn through the air intake port 113 and, thus, can stably increase the sizes of the first droplet 13*a* containing the first particulate 11*a* and the second droplet 13*b* containing the second particulate 11*b*. As a result, the particulate collection device 200 can improve the collection efficiency of the first particulate 11*a* and the second particulate 11*b*.

Modification of Embodiment 2

A modification of Embodiment 2 is described below. According to the present modification, the method for cooling the gas by the cooling unit differs from that of Embodiment 2 described above. The present modification is described below with reference to FIG. 9, focusing on the points that differ from Embodiment 2 described above.

Configuration of Cooling Unit

Figure 9:
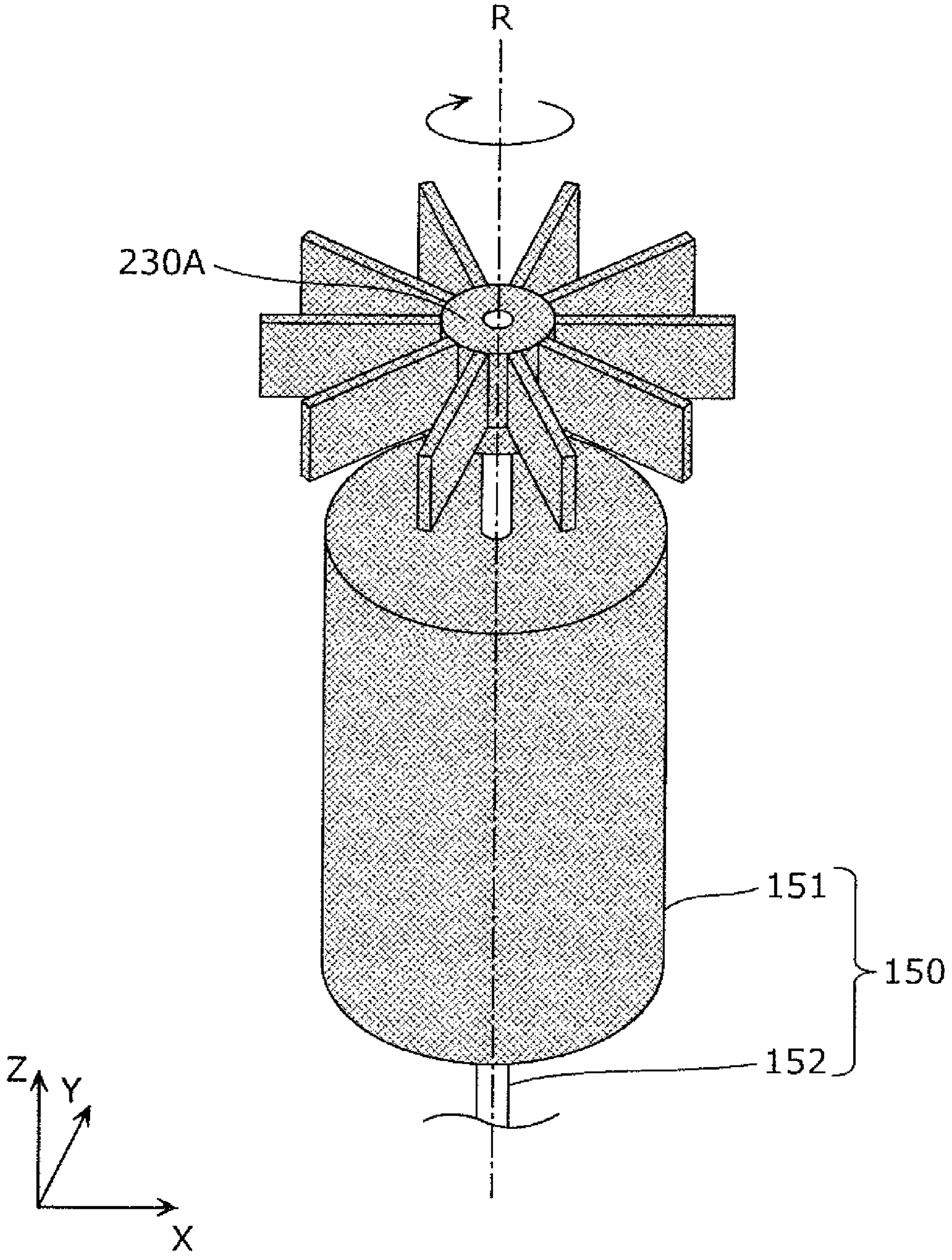
FIG. 9 is a perspective view of a cooling unit of a particulate collection device according to a modification of Embodiment 2.

FIG. 9 is a perspective view of a cooling unit 230A of a particulate collection device 200 according to the modification of Embodiment 2.

The cooling unit 230A according to the present modification cools the gas in the flow channel 115 by swirling the gas in the flow channel 115 about an axis parallel to the flow channel 115 so as to generate a pressure difference in the gas. In FIG. 9, the cooling unit 230A is composed of a blade fan.

The blade fan is connected to a shaft 152 that passes through the filter unit 151 of the first filter 150. The blade fan rotates about the R-axis together with the filter unit 151. The rotation of the blade fan swirls the gas in the flow channel 115 about the R-axis. As a result, centrifugal force is generated in the gas swirling about the R-axis, and a pressure difference is generated between the gas at the center and the gas at the periphery. As a result, the gas at the center adiabatically expands and is cooled. That is, the cooling unit 230A cools the gas by swirling the gas in the flow channel about the R-axis and generating a pressure difference in the gas. In the cooled gas at the center area, droplets 13 are formed by condensation.

Note that the cooling unit 230A is not limited to a blade fan, and any cooling unit 230A capable of swirling gas about the R-axis can be employed. For example, the cooling unit 230A may be a wall surface of the flow channel 115 that rotates about the R-axis. In this case, blades may be formed on the wall surface.

Effects

As described above, in the particulate collection device 200 according to the modification, the cooling unit 230A can cool the gas by swirling the gas in the flow channel 115 about the R-axis to generate a pressure difference in the gas.

According to the configuration, the particulate collection device 200 can cool the gas by swirling the gas. That is, the particulate collection device 200 having relatively simplified configuration can perform cooling while conserving energy. For example, when a blade fan is used to swirl the gas, the cooling unit 230 can share the rotating unit with the first filter 150 and/or the fan 141 and, thus, simplification and size reduction of the particulate collection device 200 can be achieved.

Embodiment 3

Embodiment 3 is described below. The present embodiment mainly differs from Embodiments 1 and 2 described above in that a first holding unit that holds the first particulate and a second holding unit that holds the second particulate are removable. The present embodiment is described below with reference to FIGS. 10 to 11B, focusing on the points that differ from Embodiment 1 described above.

Configuration of Particulate Collection Device

Figure 10:
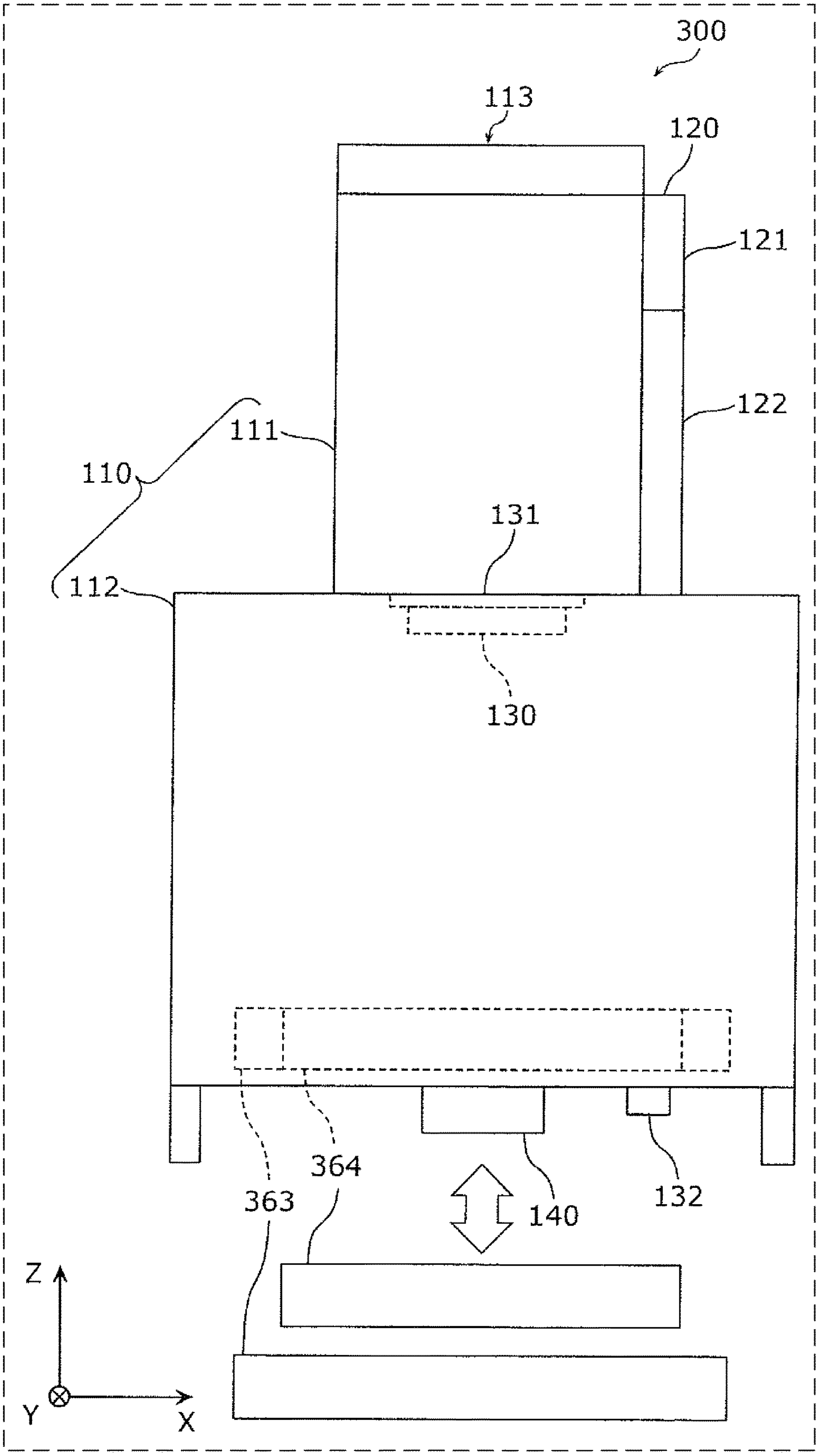
FIG. 10 is a front view of a particulate collection device according to Embodiment 3.
Figure 11A:
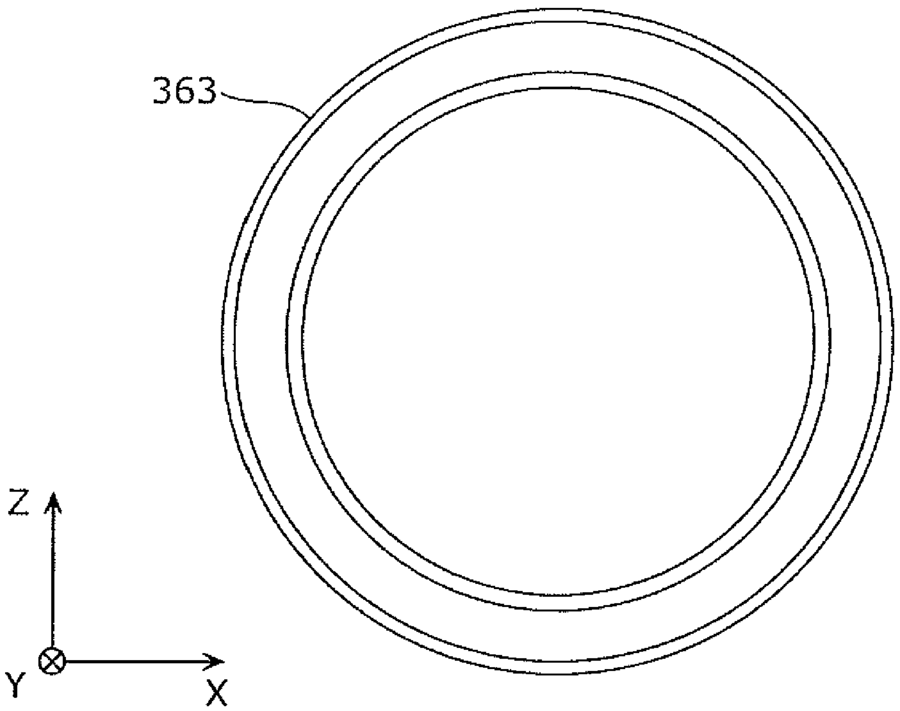
FIG. 11A is a plan view of a first holding unit according to Embodiment 3.
Figure 11B:
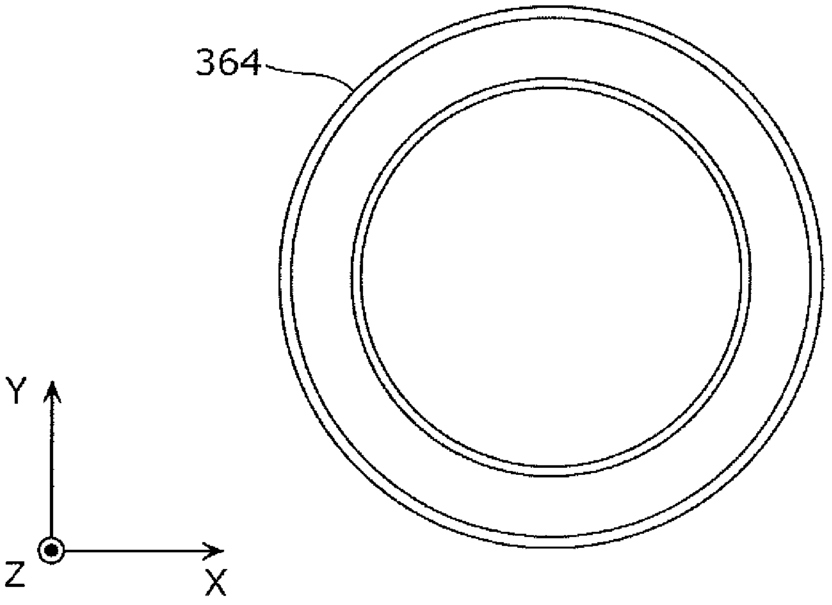
FIG. 11B is a plan view of a second holding unit according to Embodiment 3.

FIG. 10 is a front view of a particulate collection device 300 according to Embodiment 3. FIG. 11A is a plan view of a first holding unit 363 according to Embodiment 3. FIG. 11B is a plan view of a second holding unit 364 according to Embodiment 3.

The particulate collection device 300 according to the present embodiment includes the first holding unit 363 and the second holding unit 364 instead of the first holding unit 163 and the second holding unit 164, respectively. In addition, the particulate collection device 300 does not have to include the first discharge port 161 and the second discharge port 162.

As in Embodiment 1, the first holding unit 363 holds, in the first liquid 12, the first particulate 11*a* collected at the first collection port 116. The first holding unit 363 is removably provided at the top end of the first duct 118 that communicates with the first collection port 116.

As in Embodiment 1, the second holding unit 364 holds, in the first liquid 12, the second particulate 11*b* collected at the second collection port 117. The second holding unit 364 is removably provided at the top end of the second duct 119 that communicates with the second collection port 117.

As illustrated in FIG. 11A and FIG. 11B, each of the first holding unit 363 and the second holding unit 364 is a container that is circular in plan view. The diameter of the first holding unit 363 is greater than that of the second holding unit 364. In addition, as illustrated in FIG. 10, the first holding unit 363 and the second holding unit 364 are removably attached to the lower surface of the lower housing 112. Note that the shapes of the first holding unit 363 and the second holding unit 364 and a technique for removing the first holding unit 363 and the second holding unit 364 are not limited thereto. For example, each of the first holding unit 363 and the second holding unit 364 may be attached to and removed from the side surface of the lower housing 112.

According to the present embodiment, the first holding unit 363 and the second holding unit 364 are applied to the particulate collection device 100 according to Embodiment 1. However, application of the holding units is not limited thereto. That is, the first holding unit 363 and the second holding unit 364 according to the present embodiment may be applied to the particulate collection device 200 according to Embodiment 2 or the modification of Embodiment 2.

Effects

As described above, the particulate collection device 300 according to the present embodiment further includes the first holding unit 363 that holds, in the first liquid 12, the first particulate 11*a* collected at the first collection port 116 and a second holding unit 364 that holds, in the first liquid 12, the second particulate 11*b* collected at the second collection port 117. The first holding unit 363 and the second holding unit 364 are removably attached to the housing 110.

According to the configuration, the first holding unit 363 and the second holding unit 364 that hold particulates can be replaced with empty first holding unit 363 and second holding unit 364, respectively. For this reason, if there is no analyzer near the particulate collection device 300, the first holding unit 363 and the second holding unit 364 that hold the particulates can be removed and transported to the analyzer. For example, when long-term or multiple collections are made at multiple locations for investigation of environmental pollution caused by transboundary aerosols or automobile exhaust, the particulate collection device 300 is more useful because the particulate collection device 300 can collect particulates at any location.

Other Embodiments

While the particulate collection devices according to one or more aspects have been described with reference to the embodiments, the present disclosure is not limited thereto. Various modifications of the present embodiment that those skilled in the art conceive and an embodiment formed by combining the constituent elements of different embodiments without departing from the spirit of the present disclosure may be encompassed within the scope of one or more aspects of the present disclosure.

Figure 12A:
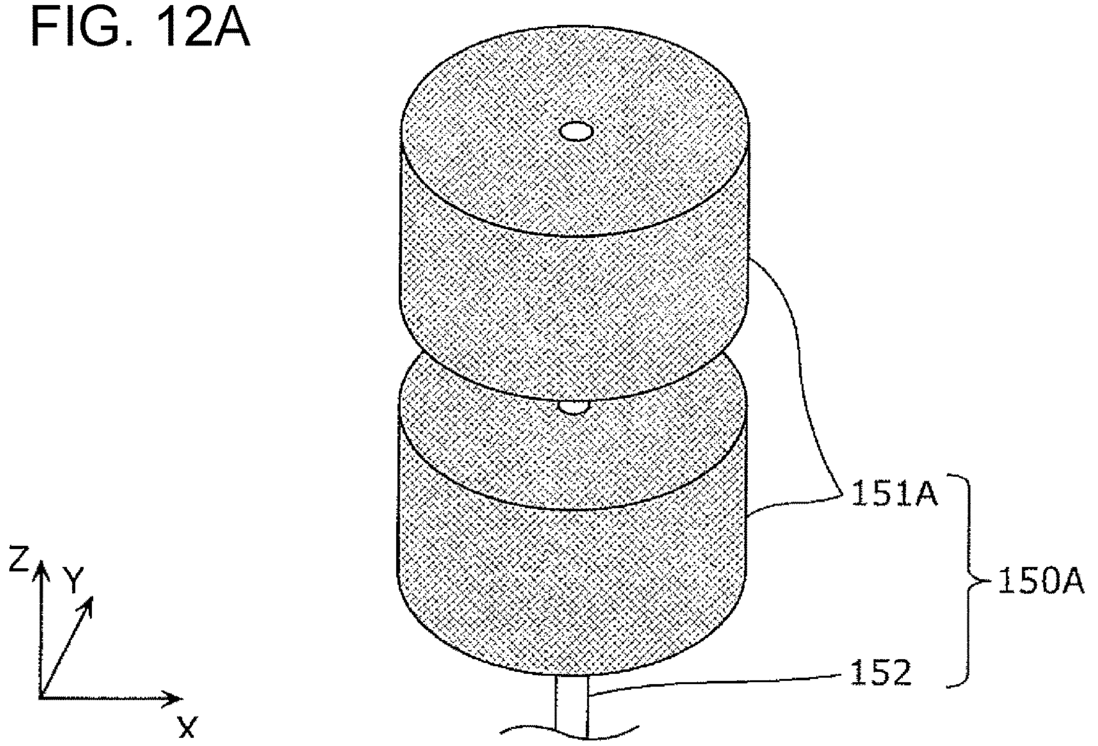
FIG. 12A is a perspective view of a filter according to another embodiment.

For example, in each of the embodiments described above, the first filter 150 includes the filter unit 151 with a single cylindrical shape. However, the configuration is not limited thereto. For example, the particulate collection device 100, 200, or 300 may be provided with a first filter 150A illustrated in FIG. 12A instead of the first filter 150. The first filter 150A includes filter units 151A each having a cylindrical shape. The filter units 151A are disposed so as to be spaced apart in the R-axis direction. At this time, the filter units 151A may be filters having different transmittance from one another. In addition, the filter units 151A may be rotated at different rotational speeds from one another. Note that in FIG. 12A, the number of the filter units 151A is two. However, the number may be three or more.

Figure 12B:
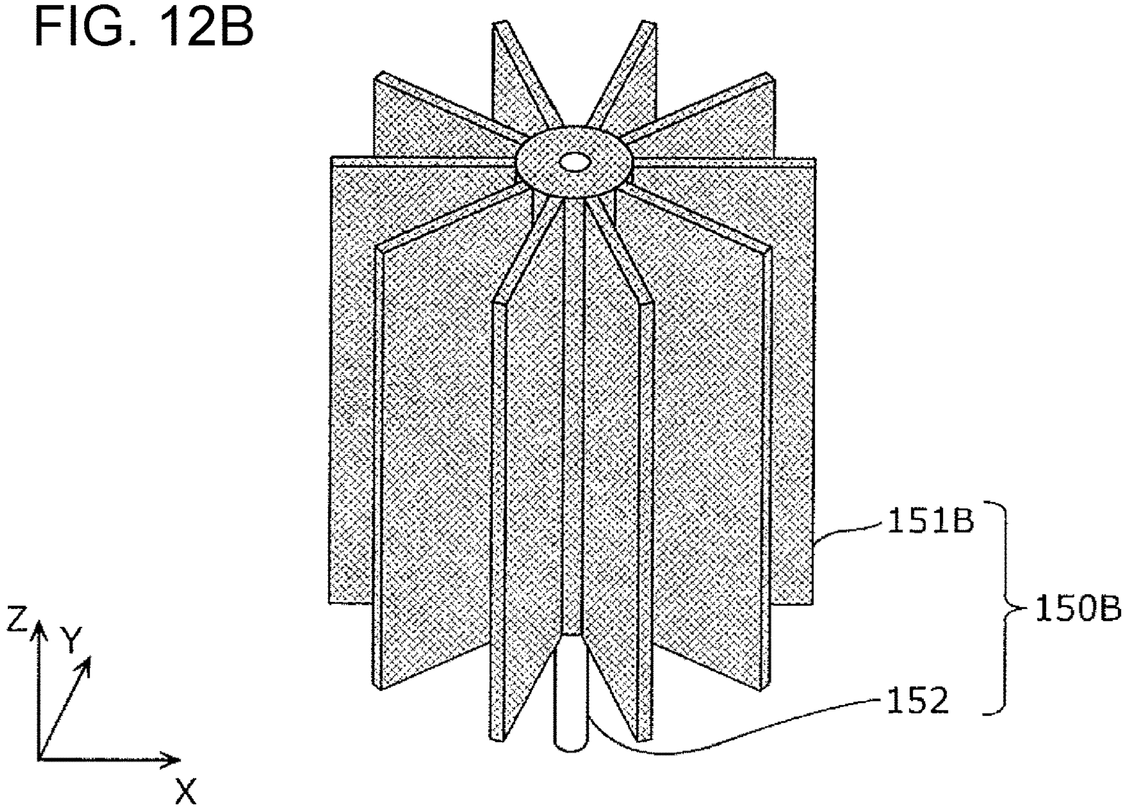
FIG. 12B is a perspective view of a filter according to another embodiment.

Alternatively, the particulate collection device 100, 200, or 300 may be equipped with a first filter 150B illustrated in FIG. 12B instead of the first filter 150. The first filter 150B includes a filter unit 151B having blades each expanding in the radial direction.

Note that the first filters 150, 150A, and 150B are only examples, and the shape of the first filter is not limited thereto.

According to the embodiments described above, each of the particulate collection devices includes a control unit. However, the particulate collection device does not necessarily have to include a control unit. In this case, the first filter may be rotated at a fixed rotational speed. Furthermore, the particulate collection device does not necessarily have to include an input unit, a first sensor, and a second sensor.

In each of the embodiments described above, the first filter and the fan are rotated by a common power source. However, the configuration is not limited thereto. For example, the first filter and the fan may be rotated by separate power sources. In this case, the particulate collection device need not include a transmission.

In each of the embodiments described above, the particulate collection device has two collection ports (the first and second collection ports). However, the number of collection ports is not limited thereto. Three or more collection ports may be provided in accordance with the number of particulate classes to be classified.

In each of the embodiments described above, the particulate collection device includes a spray unit or a pair of a humidification unit and a cooling unit. However, the particulate collection device need not include a spray unit, a humidification unit, and a cooling unit if the particulates can be coated with the liquid when they pass through the first filter.

Simulation of Trajectory of Particulate Movement in First Filter

Finally, the fact that the particulate collection device according to each of the embodiments described above can classify particulates is described based on a simple calculation of particulate movement. The conditions used in the calculation are as follows:

<Physical Property of Gas>

Viscosity $\mu$: $1.81\times10^{-5}$ [Pa·s]

<Size of First Filter>

Length L: 15 [cm]

Radius r: 5 [cm]

<Size and Density of Particulate>

Particulate diameter $D_{p1}$ of the first particulate: 4 [μm]

Particulate diameter $D_{p2}$ of the second particulate: 2 [μm]

Density of particulates $\rho_p$: 1000 [kg/m$^3$]

<Flow Velocity of Gas in Flow Channel>

Flow velocity U: 0.3 [m/s]

<Rotational speed of First Filter>

Rotational speed $\omega$: 314.2 [rad/s] (=3000 [rpm])

Under the above conditions, assuming that the forces acting on the first and second particulates are the force of the gas flowing through the channel and the resistance force due to the centrifugal force of the particulates swirled by the rotation of the first filter and the viscosity of the gas, the velocities of the first particulate and the second particulate in the first filter in the steady state can be calculated by the following equations after unit conversion:

<Velocity of Particulate>

The velocity $v_a$ of the first and second particulates in the direction of the rotation axis=U The velocity $v_{c1}$ of the first particulate in the radial direction=$(C_c\rho_p D_{p1}{}^2 r\omega^2)/(18\mu)$ The velocity $v_{c2}$ of the second particulate in the radial direction=$(C_c\rho_p D_{p2}{}^2 r\omega^2)/(18\mu)$ (where $C_c$ is the Cunningham correction factor, which can be calculated by $C_c=1+(\lambda/Dp)\times[2.514+0.800\times\exp(-0.55\times Dp/\lambda)]$. As $\lambda$ (the mean free path), 0.066 [μm] can be used.)

Figure 13:
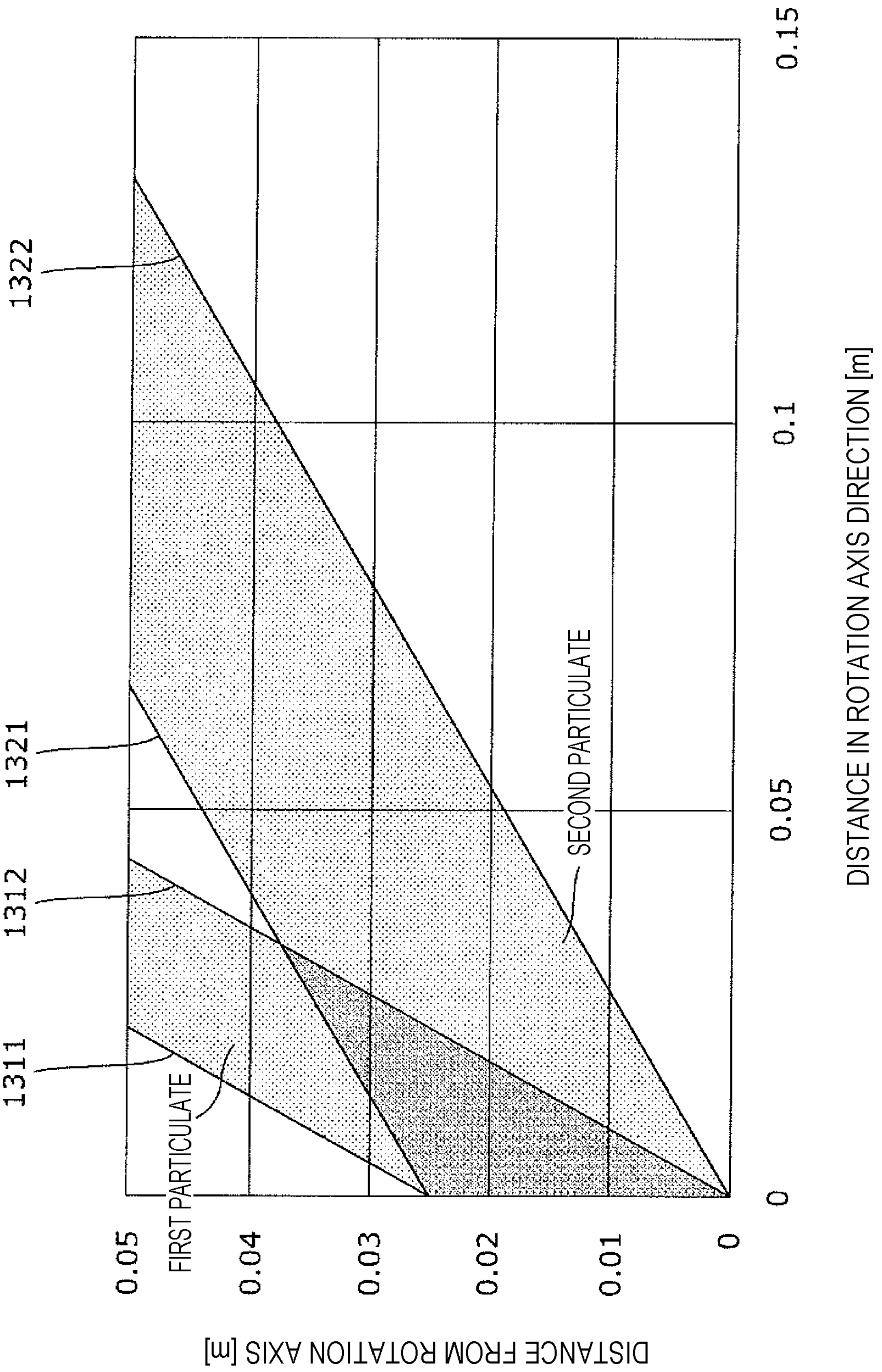
FIG. 13 is a graph denoting the simulation results of the trajectories of particulates that pass through a first filter.

FIG. 13 is a graph plotting the simulation results of the trajectories of the particulates passing through the first filter. That is, FIG. 13 illustrates the trajectories of the first and second particulates moving at the velocities obtained through the calculations described above.

FIG. 13 illustrates the trajectories 1311 and 1312 of the first particulate and the trajectories 1321 and 1322 of the second particulate. The trajectory 1311 denotes the trajectory of the first particulate that enters the first filter at a distance of 2.5 [cm] from the rotation axis of the first filter. The trajectory 1312 denotes the trajectory of the first particulate that enters the first filter at a distance of 0 [cm] from the rotation axis of the first filter. The trajectory 1321 denotes the trajectory of the second particulate that enters the first filter at a distance of 2.5 [cm] from the rotation axis of the first filter. The trajectory 1322 denotes the trajectory of the second particulate that enters the first filter at a distance of 0 [cm] from the rotation axis of the first filter.

As can be seen from FIG. 13, the trajectories of the first and second particulates are different. That is, even if the first particulate and the second particulate enter the first filter at the same position, they exit the first filter at different positions. For example, according to the trajectory 1311, the first particulate exits the first filter at a distance of 0.024 m in the direction of the rotation axis. According to the trajectory 1312, the first particulate exits the first filter at a distance of 0.042 m in the direction of the rotation axis. Therefore, it is required that the first collection port be formed in the distance range of 0.024 m to 0.042 m in the direction of the rotation axis. In addition, according to the trajectory 1321, the second particulate exits the first filter at a distance of 0.066 m in the direction of the rotation axis. According to the trajectory 1322, the second particulate exits the first filter at a distance of 0.129 m in the direction of the rotation axis. Therefore, it is required that the second collection port be formed in the distance range of 0.066 m to 0.129 m in the direction of the rotation axis.

Furthermore, as can be seen from FIG. 13, the second particulate has a wider range of a position at which the second particulate exit the first filter than the first particulate. As a result, the second particulate can be effectively collected if the length of the second collection port in the direction of the rotation axis is greater than the length of the first collection port in the direction of the rotation axis.

In addition, as is clear from the calculations described above, the velocities of the first and second particulates depend on the sizes of the first and second particulates, respectively, and the rotational speed of the first filter. Accordingly, by changing the rotational speed of the first filter, the positions at which the first and second particulates reach the wall of the flow channel, that is, the positions at which the first and second particulates leave the first filter can be changed. That is, by controlling the rotational speed of the first filter in accordance with the sizes of the first and second particulates, the control unit can effectively cause the first and second particulates to reach the first and second collection ports, respectively.

Note that the calculations described above do not take into account the deceleration of the particulates in the direction of the rotation axis due to collision with the first filter. However, because the particulate decelerates more strongly with increasing size thereof, classification of the particulates into the first and second particulates is facilitated more if the deceleration is taken into account.

The present disclosure is widely applicable to devices for sampling particulates in the air.

What is claimed is:

1. A particulate collection device comprising:

a housing having an air intake port, an exhaust port, and a flow channel connecting the air intake port to the exhaust port in the housing;

a fan that generates, in the flow channel, airflow for drawing, from the air intake port into the flow channel, a gas containing a first particulate and a second particulate smaller than the first particulate, the fan being rotatable about a first axis;

a sprayer that sprays a first liquid into a first portion included in the flow channel to coat the first particulate with liquid contained in the first liquid and coat the second particulate with liquid contained in the first liquid;

a first filter located between the first portion and the exhaust port and supported rotatably about the first axis;

a power source that rotates the first filter;

a first collection port used to collect the first particulate coated with the liquid contained in the first liquid from the flow channel through a second portion included in the first filter;

a second collection port used to collect the second particulate coated with the liquid contained in the first liquid from the flow channel through a third portion included in the first filter;

a controller configured to control a rotational speed of the first filter; and a first sensor configured to detect a particulate having a particulate size greater than or equal to a first predetermined particulate size in a gas output from the exhaust port, wherein the second portion is located between the first portion and the third portion, and wherein the controller is configured to increase the rotational speed of the first filter when the first sensor detects the particulate.

2. The particulate collection device according to claim 1, further comprising:

a first discharge port used to discharge, to an outside of the housing, the first particulate and the liquid contained in the first liquid and coating the first particulate, the first particulate and the liquid being collected at the first collection port; and a second discharge port used to discharge, to the outside of the housing, the second particulate and the liquid contained in the first liquid and coating the second particulate, the second particulate and the liquid being collected at the second collection port.

3. The particulate collection device according to claim 1, further comprising:

a first holder that holds, in the first liquid, the first particulate collected at the first collection port; and a second holder that holds, in the first liquid, the second particulate collected at the second collection port, wherein the first holder and the second holder are removably attached to the housing.

4. The particulate collection device according to claim 1, wherein the first liquid is liquid used to analyze the first particulate and the second particulate.

5. The particulate collection device according to claim 1, further comprising:

a second sensor configured to detect a concentration of particulates each having a particulate size greater than or equal to a second predetermined particulate size in a gas drawn into the air intake port, wherein the controller has a standby mode in which rotation of the first filter and spraying performed by the sprayer are stopped and the fan is rotated, and wherein in the standby mode, the controller is configured to deactivate the standby mode to start the rotation of the first filter and the spraying performed by the sprayer when the concentration of the particulates detected by the second sensor is higher than or equal to a threshold concentration.

6. A particulate collection device comprising:

a housing having an air intake port, an exhaust port, and a flow channel connecting the air intake port to the exhaust port in the housing;

a fan that generates, in the flow channel, airflow for drawing, from the air intake port into the flow channel, a gas containing a first particulate and a second particulate smaller than the first particulate, the fan being rotatable about a first axis;

a sprayer that sprays a first liquid into a first portion included in the flow channel to coat the first particulate with liquid contained in the first liquid and coat the second particulate with liquid contained in the first liquid;

a first filter located between the first portion and the exhaust port and supported rotatably about the first axis;

a power source that rotates the first filter;

a first collection port used to collect the first particulate coated with the liquid contained in the first liquid from the flow channel through a second portion included in the first filter;

a second collection port used to collect the second particulate coated with the liquid contained in the first liquid from the flow channel through a third portion included in the first filter; and a second filter removably attached to the air intake port and preventing the first particulate and the second particulate from entering the flow channel, wherein the second portion is located between the first portion and the third portion, and wherein the sprayer sprays a second liquid to clean the first filter and the flow channel when the second filter is attached.

7. A particulate collection device comprising:
a housing having an air intake port, an exhaust port, and a flow channel connecting the air intake port to the exhaust port in the housing;
a fan that generates, in the flow channel, airflow for drawing, from the air intake port into the flow channel, a gas containing a first particulate and a second particulate smaller than the first particulate, the fan being rotatable about a first axis;
a sprayer that sprays a first liquid into a first portion included in the flow channel to coat the first particulate with liquid contained in the first liquid and coat the second particulate with liquid contained in the first liquid;
a first filter located between the first portion and the exhaust port and supported rotatably about the first axis;
a power source that rotates the first filter;
a first collection port used to collect the first particulate coated with the liquid contained in the first liquid from the flow channel through a second portion included in the first filter;
a second collection port used to collect the second particulate coated with the liquid contained in the first liquid from the flow channel through a third portion included in the first filter;
a controller configured to control a rotational speed of the first filter; and
an inputter that receives information on respective sizes of the first particulate and the second particulate input by a user,
wherein the controller is configured to control the rotational speed of the first filter based on the input information.

* * * * *

UNITED STATES PATENT AND TRADEMARK OFFICE
CERTIFICATE OF CORRECTION

PATENT NO. : 12,157,083 B2  
APPLICATION NO. : 17/368985  
DATED : December 3, 2024  
INVENTOR(S) : Koki Narihata Page 1 of 1

It is certified that error appears in the above-identified patent and that said Letters Patent is hereby corrected as shown below:

On the Title Page

In item (73) Assignee: change "INTELLECTUAL PROPERTY MANAGEMENT CO., LTD., Osaka (JP)" to -- PANASONIC INTELLECTUAL PROPERTY MANAGEMENT CO., LTD., Osaka (JP) --.

Signed and Sealed this
Eleventh Day of March, 2025

Coke Morgan Stewart
*Acting Director of the United States Patent and Trademark Office*